(12) United States Patent
Luciano

(10) Patent No.: US 10,315,450 B1
(45) Date of Patent: Jun. 11, 2019

(54) SYSTEM AND METHOD FOR GENERATING AN INTEGRATED LABEL FOR CONTAINER HOUSING MULTI-SCRIPT POUCHES

(75) Inventor: Robert A. Luciano, Reno, NV (US)

(73) Assignee: Edge Medical Properties, LLC, Reno, NV (US)

( * ) Notice: Subject to any disclaimer, the term of this patent is extended or adjusted under 35 U.S.C. 154(b) by 27 days.

(21) Appl. No.: 12/896,284

(22) Filed: Oct. 1, 2010

Related U.S. Application Data

(63) Continuation-in-part of application No. 12/696,884, filed on Jan. 29, 2010, which is a continuation of application No. 11/923,321, filed on Oct. 24, 2007, now Pat. No. 8,266,878, application No. 12/896,284, which is a continuation-in-part of application No. 12/891,029, filed on Sep. 27, 2010, which is a continuation-in-part of application No. 12/424,475, filed on Apr. 15, 2009, now Pat. No. 8,146,747.

(60) Provisional application No. 61/248,471, filed on Oct. 4, 2009, provisional application No. 60/854,341, filed on Oct. 24, 2006, provisional application No. 61/245,899, filed on Sep. 25, 2009, provisional application No. 61/045,160, filed on Apr. 15, 2008, provisional application No. 61/045,166, filed on Apr. 15, 2008, provisional application No. 61/045,171, filed on Apr. 15, 2008.

(51) Int. Cl.
| | |
|---|---|
| *B42D 1/00* | (2006.01) |
| *B42D 19/00* | (2006.01) |
| *B42D 15/00* | (2006.01) |
| *G09C 3/00* | (2006.01) |

(52) U.S. Cl.
CPC ............... *B42D 1/00* (2013.01); *B42D 19/00* (2013.01); *B42D 15/00* (2013.01); *G09C 3/00* (2013.01)

(58) Field of Classification Search
CPC .......... B42D 1/00; B42D 19/00; B42D 15/00; B42D 15/10; G09C 3/00; A61J 7/0076; A61J 7/02; A61J 7/04; A61J 7/0084; A61J 2205/00; B65D 83/00
USPC .... 281/2, 3.1, 5; 283/56, 61, 62, 72, 74, 75, 283/77, 81; 53/411
See application file for complete search history.

(56) References Cited

U.S. PATENT DOCUMENTS

| | | | |
|---|---|---|---|
| 2,294,220 | A | 8/1942 | Albertson |
| 3,126,129 | A | 3/1964 | Weinberg |
| 3,254,828 | A | 6/1966 | Lerner |
| 3,308,962 | A | 3/1967 | Bryant |
| 3,409,721 | A | 11/1968 | Norman |

(Continued)

FOREIGN PATENT DOCUMENTS

| | | |
|---|---|---|
| DE | 3502647 A1 | 7/1986 |
| WO | WO 96/13790 A1 | 5/1996 |

(Continued)

*Primary Examiner* — Justin V Lewis
(74) *Attorney, Agent, or Firm* — Michael A. Kerr; Kerr IP Group, LLC

(57) ABSTRACT

A system for integrating and labeling a plurality of tablet orders is described. The system comprises a graphical user interface configured to receive one or more inputs for a plurality of tablets associated with a particular patient. A software module is configured to compile the inputs into an integrated order. The system further comprises an integrated label coupled to a package containing a dose comprised of the plurality of tablets input into the graphical user interface. The integrated label indicates information about the first dose and the second dose.

18 Claims, 37 Drawing Sheets

(56) References Cited

U.S. PATENT DOCUMENTS

| | | |
|---|---|---|
| 3,410,450 A | 11/1968 | Fortenberry |
| 3,432,951 A | 3/1969 | Cherrin |
| 3,450,306 A | 6/1969 | Gill |
| 3,497,982 A | 3/1970 | Schulz |
| 3,503,493 A | 3/1970 | Nagy |
| 3,703,955 A | 11/1972 | Inacker |
| 3,773,250 A | 11/1973 | Phillips |
| 3,780,856 A | 12/1973 | Braverman |
| 3,809,220 A | 5/1974 | Arcudi |
| 3,881,625 A | 5/1975 | James |
| 3,884,379 A | 5/1975 | James |
| 3,921,804 A | 11/1975 | Tester |
| 3,033,245 A | 1/1976 | Mullen |
| 4,036,385 A | 7/1977 | Morris |
| 4,039,080 A | 8/1977 | Cappuccilli |
| 4,062,445 A | 12/1977 | Moe |
| 4,274,550 A | 6/1981 | Feldstein |
| 4,318,477 A | 3/1982 | Kerpe |
| 4,416,375 A | 11/1983 | Braverman et al. |
| 4,512,476 A | 4/1985 | Herrington, Jr. |
| 4,535,890 A | 8/1985 | Artusi |
| 4,546,901 A | 10/1985 | Buttarazzi |
| 4,553,670 A | 11/1985 | Collens |
| 4,635,890 A | 1/1987 | Matsuda et al. |
| 4,655,026 A | 4/1987 | Wigoda |
| 4,693,371 A | 9/1987 | Malpass |
| 4,733,797 A | 3/1988 | Haber |
| 4,736,849 A | 4/1988 | Leonard et al. |
| 4,749,085 A | 6/1988 | Denney |
| 4,799,590 A | 1/1989 | Furman |
| 4,805,800 A | 2/1989 | Nocek et al. |
| 4,811,764 A | 3/1989 | McLaughlin |
| 4,823,982 A | 4/1989 | Aten et al. |
| 4,830,183 A | 5/1989 | Metters |
| 4,832,229 A | 5/1989 | Hackmann et al. |
| 4,850,489 A | 7/1989 | Weithmann et al. |
| 4,860,899 A | 8/1989 | McKee |
| 4,867,315 A | 9/1989 | Baldwin |
| 4,872,559 A | 10/1989 | Schoon |
| 4,872,593 A | 10/1989 | Behringer |
| 4,887,790 A | 12/1989 | Wilkinson et al. |
| 4,918,604 A | 4/1990 | Baum |
| 4,953,745 A | 9/1990 | Rowlett, Jr. |
| 4,954,210 A | 9/1990 | Desmond |
| 4,972,657 A * | 11/1990 | McKee ............... A61J 7/0076 53/168 |
| 4,993,586 A | 2/1991 | Taulbee et al. |
| 5,014,851 A | 5/1991 | Wick |
| 5,027,954 A | 7/1991 | Hickerson |
| 5,085,510 A | 2/1992 | Mitchell |
| 5,186,345 A | 2/1993 | Ching An |
| 5,195,123 A | 3/1993 | Clement |
| 5,199,636 A | 4/1993 | Young |
| 5,310,057 A | 5/1994 | Caldwell et al. |
| 5,310,437 A | 5/1994 | Tucker |
| 5,366,087 A | 11/1994 | Bane |
| 5,390,796 A | 2/1995 | Kerfoot, Jr. |
| 5,422,831 A | 6/1995 | Misra et al. |
| 5,443,178 A | 8/1995 | Holmes |
| 5,457,895 A | 10/1995 | Thompson et al. |
| 5,505,371 A | 4/1996 | O'Neill |
| 5,522,512 A | 6/1996 | Archer et al. |
| 5,544,768 A | 8/1996 | Gargione |
| 5,558,229 A | 9/1996 | Halbich |
| 5,577,612 A | 11/1996 | Chesson et al. |
| 5,597,995 A | 1/1997 | Williams et al. |
| 5,642,906 A | 7/1997 | Foote et al. |
| 5,671,592 A | 9/1997 | Yuyama et al. |
| 5,711,442 A | 1/1998 | Kusz |
| 5,737,539 A | 4/1998 | Edelson et al. |
| 5,746,323 A | 5/1998 | Dragotta |
| 5,788,079 A | 8/1998 | Bouthiette |
| 5,788,974 A | 8/1998 | Maida |
| 5,792,092 A | 8/1998 | Turngren |
| D400,412 S | 11/1998 | Gold |
| 5,873,466 A | 2/1999 | Hulick |
| 5,878,887 A | 3/1999 | Parker et al. |
| 5,883,370 A | 3/1999 | Walker et al. |
| 5,891,078 A | 4/1999 | Turngren et al. |
| 5,899,333 A | 5/1999 | Williams et al. |
| 5,921,398 A | 7/1999 | Carroll |
| 5,941,402 A | 8/1999 | Krueger |
| 5,963,453 A | 10/1999 | East |
| 5,995,938 A | 11/1999 | Whaley |
| 6,012,582 A | 1/2000 | Haygeman et al. |
| 6,021,392 A | 2/2000 | Lester et al. |
| 6,021,623 A | 2/2000 | Bouthiette |
| 6,023,916 A | 2/2000 | Bouthiette |
| 6,066,374 A | 5/2000 | Healy et al. |
| 6,068,156 A | 5/2000 | Liff et al. |
| 6,077,530 A | 6/2000 | Weinstein et al. |
| 6,115,996 A | 9/2000 | Yuyama et al. |
| 6,129,211 A | 10/2000 | Prakken et al. |
| 6,155,423 A | 12/2000 | Katzner et al. |
| 6,155,485 A | 12/2000 | Coughlin et al. |
| 6,170,230 B1 | 1/2001 | Chudy et al. |
| 6,171,439 B1 | 1/2001 | Groeneweg |
| 6,181,979 B1 | 1/2001 | Murakami |
| 6,202,923 B1 | 3/2001 | Boyer et al. |
| 6,213,343 B1 | 4/2001 | Damikolas |
| 6,227,371 B1 | 5/2001 | Song |
| 6,273,260 B1 | 8/2001 | ColDepietro et al. |
| 6,293,403 B1 | 9/2001 | Holmberg |
| 6,308,494 B1 | 10/2001 | Yuyama et al. |
| 6,317,648 B1 | 11/2001 | Sleep et al. |
| 6,318,630 B1 | 11/2001 | Coughlin et al. |
| 6,324,253 B1 | 11/2001 | Yuyama et al. |
| 6,330,351 B1 | 12/2001 | Yasunaga |
| 6,343,695 B1 | 2/2002 | Petrick et al. |
| D455,057 S | 4/2002 | Medhurst |
| 6,371,297 B1 | 4/2002 | Cha |
| 6,375,956 B1 | 4/2002 | Hermelin et al. |
| 6,378,572 B1 | 4/2002 | Neubauer et al. |
| 6,401,919 B1 | 6/2002 | Griffis et al. |
| 6,449,921 B1 | 9/2002 | Kim |
| 6,449,927 B2 | 9/2002 | Hebron et al. |
| 6,460,693 B1 | 10/2002 | Harrold |
| 6,505,461 B1 | 1/2003 | Yasunaga |
| 6,523,694 B2 | 2/2003 | Lux, Jr. et al. |
| 6,527,138 B2 | 3/2003 | Pawlo et al. |
| 6,535,637 B1 | 3/2003 | Wootton et al. |
| 6,581,798 B2 | 6/2003 | Liff et al. |
| 6,594,928 B1 | 7/2003 | Clawson et al. |
| 6,611,733 B1 | 8/2003 | Huerga |
| 6,662,081 B1 | 12/2003 | Jacober et al. |
| 6,681,935 B1 | 1/2004 | Lewis |
| 6,690,998 B1 | 2/2004 | Yuyama |
| 6,711,460 B1 | 3/2004 | Reese |
| 6,735,497 B2 | 5/2004 | Wallace et al. |
| 6,738,723 B2 | 5/2004 | Hamilton |
| 6,757,898 B1 | 6/2004 | Ilsen et al. |
| 6,771,369 B2 | 8/2004 | Rzasa |
| 6,839,403 B1 | 1/2005 | Kotowski et al. |
| 6,892,512 B2 | 5/2005 | Rice et al. |
| 6,925,774 B2 | 8/2005 | Peterson |
| 6,962,266 B2 | 11/2005 | Morgan et al. |
| 6,981,592 B2 | 1/2006 | Siegel |
| 7,006,893 B2 | 2/2006 | Hart et al. |
| 7,010,899 B2 | 3/2006 | McErlean et al. |
| 7,017,513 B2 | 3/2006 | Giewercer |
| 7,017,748 B2 | 3/2006 | Weinstein |
| 7,028,723 B1 | 4/2006 | Alouani et al. |
| 7,055,294 B1 | 6/2006 | Lewis |
| 7,089,131 B2 | 8/2006 | Thouin et al. |
| 7,111,780 B2 | 9/2006 | Broussard et al. |
| 7,185,476 B1 | 3/2007 | Siegel et al. |
| 7,225,597 B1 | 6/2007 | Knoth |
| 7,398,279 B2 | 7/2008 | Muno et al. |
| 7,426,814 B2 | 9/2008 | Knoth |
| 7,509,787 B2 | 3/2009 | Ballestrazzi et al. |
| 7,559,482 B2 | 7/2009 | Coveley |
| 7,568,580 B2 | 8/2009 | Fenton |
| 7,668,730 B2 | 2/2010 | Reardan et al. |
| 7,747,345 B2 | 6/2010 | Ohmura et al. |

(56) References Cited

U.S. PATENT DOCUMENTS

| | | | |
|---|---|---|---|
| 7,828,148 B2 | 11/2010 | Gibson | |
| 7,942,280 B2 | 5/2011 | Priebe et al. | |
| 7,942,451 B2 | 5/2011 | Adler | |
| 7,946,421 B2 | 5/2011 | Kowalik et al. | |
| 8,020,702 B2 | 9/2011 | Strub et al. | |
| 8,041,102 B2 | 10/2011 | Yuyama et al. | |
| 8,055,512 B1 | 11/2011 | Pankow et al. | |
| 8,074,426 B2 | 12/2011 | Luciano et al. | |
| 8,122,849 B2 | 2/2012 | Clarke et al. | |
| 8,123,036 B2 | 2/2012 | Luciano et al. | |
| 8,146,747 B2 | 4/2012 | Luciano et al. | |
| 8,196,774 B1 | 6/2012 | Clarke et al. | |
| 8,266,878 B2 | 9/2012 | Luciano et al. | |
| 8,556,077 B1 | 10/2013 | Hanley | |
| 8,712,582 B1 | 4/2014 | Luciano et al. | |
| 8,713,897 B2 | 5/2014 | Luciano et al. | |
| 8,752,704 B2 | 6/2014 | Alonso et al. | |
| 8,777,012 B2 | 7/2014 | Luciano et al. | |
| 8,789,700 B2 | 7/2014 | Luciano et al. | |
| 8,914,298 B1 | 12/2014 | Luciano | |
| 8,931,241 B2 | 1/2015 | Luciano et al. | |
| 8,972,288 B2 | 3/2015 | Luciano | |
| 9,334,096 B2 | 5/2016 | Luciano et al. | |
| 9,428,314 B2 | 8/2016 | Luciano et al. | |
| 2001/0041968 A1 | 11/2001 | Hamilton | |
| 2002/0029223 A1 | 3/2002 | Rice et al. | |
| 2002/0042725 A1 | 4/2002 | Mayaud | |
| 2002/0047019 A1 | 4/2002 | Devers | |
| 2002/0066691 A1 | 6/2002 | Varon | |
| 2002/0104778 A1 | 8/2002 | Lux et al. | |
| 2002/0117405 A1 | 8/2002 | Wang et al. | |
| 2003/0012701 A1 | 1/2003 | Sangha et al. | |
| 2003/0018495 A1 | 1/2003 | Sussman | |
| 2003/0136698 A1 | 7/2003 | Klatt | |
| 2003/0142784 A1 | 7/2003 | Suzuki et al. | |
| 2003/0174326 A1 | 9/2003 | Rzasa et al. | |
| 2003/0193185 A1 | 10/2003 | Valley et al. | |
| 2003/0200726 A1 | 10/2003 | Rast | |
| 2003/0209461 A1 | 11/2003 | French et al. | |
| 2004/0011806 A1* | 1/2004 | Luciano et al. | 221/266 |
| 2004/0011961 A1 | 1/2004 | Platt et al. | |
| 2004/0045863 A1 | 3/2004 | Rhoades | |
| 2004/0069674 A1 | 4/2004 | Siegel | |
| 2004/0069675 A1 | 4/2004 | Stevens | |
| 2004/0088187 A1 | 5/2004 | Chudy et al. | |
| 2004/0094050 A1 | 5/2004 | Ackley et al. | |
| 2004/0122713 A1 | 6/2004 | Hill, Sr. et al. | |
| 2004/0123564 A1 | 7/2004 | McErlean et al. | |
| 2004/0140241 A1 | 7/2004 | Weinstein | |
| 2004/0158507 A1 | 8/2004 | Meek et al. | |
| 2004/0162634 A1 | 8/2004 | Rice et al. | |
| 2004/0172295 A1 | 9/2004 | Dahlin et al. | |
| 2004/0188998 A1* | 9/2004 | Henthorn | A61J 7/04 283/115 |
| 2004/0217038 A1 | 11/2004 | Gibson | |
| 2004/0225528 A1 | 11/2004 | Brock | |
| 2004/0243445 A1 | 12/2004 | Keene | |
| 2004/0249591 A1 | 12/2004 | Trebbi | |
| 2004/0251157 A1 | 12/2004 | Behnke et al. | |
| 2004/0256277 A1 | 12/2004 | Gedanke | |
| 2004/0260424 A1 | 12/2004 | Mahar | |
| 2004/0268413 A1 | 12/2004 | Reid et al. | |
| 2005/0021367 A1 | 1/2005 | Saeger et al. | |
| 2005/0044762 A1 | 3/2005 | Atluri | |
| 2005/0049746 A1 | 3/2005 | Rosenblum | |
| 2005/0049747 A1 | 3/2005 | Willoughby et al. | |
| 2005/0060197 A1 | 3/2005 | Mayaud | |
| 2005/0061825 A1 | 3/2005 | Willoughby et al. | |
| 2005/0144038 A1 | 6/2005 | Tamblyn et al. | |
| 2005/0171813 A1 | 8/2005 | Jordan | |
| 2005/0209879 A1 | 9/2005 | Chalmers | |
| 2005/0218152 A1 | 10/2005 | Simon | |
| 2005/0269817 A1* | 12/2005 | Alasia et al. | 283/73 |
| 2006/0045323 A1 | 3/2006 | Ateya | |
| 2006/0064670 A1 | 3/2006 | Linebarger et al. | |
| 2006/0065670 A1 | 3/2006 | Doublet et al. | |
| 2006/0076262 A1 | 4/2006 | Bassett | |
| 2006/0086640 A1 | 4/2006 | Luciano et al. | |
| 2006/0122729 A1 | 6/2006 | Murphy et al. | |
| 2006/0124502 A1 | 6/2006 | Lee | |
| 2006/0163269 A1 | 7/2006 | Anderson et al. | |
| 2006/0163869 A1* | 7/2006 | Adler | G09F 3/0288 283/81 |
| 2006/0213816 A1 | 9/2006 | Jorritsma | |
| 2006/0219595 A1 | 10/2006 | Peters | |
| 2007/0000805 A1 | 1/2007 | Brink | |
| 2007/0131576 A1 | 6/2007 | Ehling et al. | |
| 2007/0150219 A1 | 6/2007 | Cawker et al. | |
| 2007/0168228 A1 | 7/2007 | Lawless | |
| 2007/0169838 A1 | 7/2007 | Yuyama et al. | |
| 2007/0173971 A1 | 7/2007 | Richardson et al. | |
| 2007/0210164 A1 | 9/2007 | Conlon et al. | |
| 2007/0228047 A1 | 10/2007 | Pehr et al. | |
| 2007/0235369 A1 | 10/2007 | Perell | |
| 2008/0010848 A1 | 1/2008 | Miles | |
| 2008/0059228 A1 | 3/2008 | Bossi et al. | |
| 2008/0110131 A1 | 5/2008 | Kim | |
| 2008/0142400 A1 | 6/2008 | Arnold | |
| 2008/0190076 A1 | 8/2008 | Klingel et al. | |
| 2008/0228160 A1 | 9/2008 | Harrison | |
| 2009/0119129 A1 | 5/2009 | Nadas et al. | |
| 2009/0133362 A1 | 5/2009 | Bentele et al. | |
| 2009/0139893 A1 | 6/2009 | McGonagle et al. | |
| 2009/0230013 A1 | 9/2009 | Born et al. | |
| 2009/0301925 A1 | 12/2009 | Alloro | |
| 2010/0069213 A1 | 3/2010 | Luciano et al. | |
| 2010/0089936 A1 | 4/2010 | Luciano et al. | |
| 2010/0100391 A1 | 4/2010 | Daya et al. | |
| 2010/0139222 A1 | 6/2010 | Federle et al. | |
| 2010/0147734 A1 | 6/2010 | Luciano et al. | |
| 2010/0175352 A1* | 7/2010 | Soloman | B65B 5/103 53/508 |
| 2010/0252479 A1 | 10/2010 | Corroon | |
| 2010/0265072 A1 | 10/2010 | Goetz et al. | |
| 2010/0287880 A1 | 11/2010 | Yasunaga et al. | |
| 2010/0324728 A1 | 12/2010 | Rosenblum | |
| 2011/0015576 A1 | 1/2011 | Plumptre et al. | |
| 2011/0036856 A1 | 2/2011 | Ooyen et al. | |
| 2011/0040572 A1 | 2/2011 | Chmiel et al. | |
| 2011/0100863 A1 | 5/2011 | Luciano | |
| 2011/0101016 A1 | 5/2011 | Luciano | |
| 2011/0157342 A1 | 6/2011 | Kim | |
| 2011/0161097 A1 | 6/2011 | Fox et al. | |
| 2011/0251850 A1 | 10/2011 | Stephens | |
| 2011/0264465 A1 | 10/2011 | Lindsay | |
| 2012/0022893 A1 | 1/2012 | Findlay et al. | |
| 2012/0089416 A1 | 4/2012 | Luciano | |
| 2012/0097560 A1 | 4/2012 | Contractor | |
| 2012/0116579 A1 | 5/2012 | Shows et al. | |
| 2012/0123907 A1 | 5/2012 | Luciano | |
| 2012/0145585 A1 | 6/2012 | Doyle et al. | |
| 2012/0145739 A1 | 6/2012 | Doyle et al. | |
| 2012/0158430 A1 | 6/2012 | MacDonald | |
| 2012/0186693 A1 | 7/2012 | Luciano et al. | |
| 2012/0200596 A1 | 8/2012 | Gotou et al. | |
| 2012/0290129 A1 | 11/2012 | Luciano et al. | |
| 2012/0293623 A1 | 11/2012 | Nygaard | |
| 2012/0296592 A1 | 11/2012 | Luciano et al. | |
| 2012/0312714 A1 | 12/2012 | Luciano et al. | |
| 2013/0161207 A1 | 6/2013 | Luciano et al. | |
| 2014/0002631 A1 | 1/2014 | Amano et al. | |

FOREIGN PATENT DOCUMENTS

| | | |
|---|---|---|
| WO | WO 2004/082561 A1 | 9/2004 |
| WO | WO 2005/102841 | 11/2005 |
| WO | 2011080462 A1 | 7/2011 |

* cited by examiner

FIGURE 10

SYSTEM AND METHOD FOR GENERATING AN INTEGRATED LABEL FOR CONTAINER HOUSING MULTI-SCRIPT POUCHES

CROSS-REFERENCE TO RELATED PATENT APPLICATIONS

The present patent application claims the priority of provisional patent application No. 61/248,471, filed Oct. 4, 2009; and this patent application is a continuation-in-part of patent application Ser. No. 12/696,884, filed Jan. 29, 2010, which is a continuation of patent application Ser. No. 11/923,321, filed Oct. 24, 2007 (now U.S. Pat. No. 8,266,878), which claims the benefit of provisional patent application No. 60/854,341, filed Oct. 24, 2006; and this patent application is a continuation-in-part of patent application Ser. No. 12/891,029, filed Sep. 27, 2010, which claims the benefit of provisional patent application No. 61/245,899, filed Sep. 25, 2009, additionally patent application Ser. No. 12/981,029 is a continuation-in-part of patent application Ser. No. 12/424,475, filed Apr. 15, 2009 (now U.S. Pat. No. 8,146,747), which claims the benefit of provisional application No. 61/045,160, filed Apr. 15, 2008, provisional application No. 61/045,166, filed Apr. 15, 2008, and provisional application No. 61/045,171, filed Apr. 15, 2008.

FIELD OF THE INVENTION

The invention relates to a system and method for integrating and labeling a plurality of tablet orders. More particularly, the invention relates to generating an integrated order from multiple tablet orders and labeling a package containing an integrated order with information about the tablets contained in the package.

BACKGROUND

There are a variety of problems encountered by individuals taking multiple prescription medications simultaneously. A principal concern is determining whether all medications have been taken in compliance with the prescribed daily regimen. Many times this concern is compounded by the requirement that portions of the various medications must be taken at different times during the day as well as in different amounts or quantities. For instance, some individuals, e.g., those suffering from certain psychological disorders, may require varying quantities of a particular medication. For example, a patient receiving lithium may require a low dosage of the medication when administration begins (e.g., 200 mg). However, as the patient's treatment continues, stronger doses (e.g., 300 mg) may be prescribed as the patient's levels are titrated upward from the starting level. Thus, a patient receiving lithium may be prescribed a single 200 mg pill for the first three days of treatment, whereafter stronger pills, or additional doses of weaker pills, are prescribed.

The fear of taking improper dosages of prescribed medications can be particularly acute in the elderly, many of whom have some degree of mental dementia and can easily be confused as to whether they have taken all of their mediations at the correct time. Some patients with limited mental abilities have difficulty simply sorting their various medications in preparation for taking them and, thereafter, taking them in a timely manner (i.e., in compliance with their dosing cycle). Providing medications to disabled and/or incapacitated individuals can also be a problem for caregivers, particularly those in hospitals and assisted living facilities where one caregiver may oversee the medication of many patients.

Thus, there is a need for an automated system for ordering and integrating multiple prescription medications, whereby patients may receive consolidated groups of medications for administration (e.g., usually, consumption) at prescribed dosing intervals and in prescribed, possibly varying, quantities. Such a system would decrease the possibility of human error and provide a simple mechanism for the correct selection, verification, integration, packaging and delivery of multiple prescription medications (also referred to as "multi-scripts").

There is also a need for a similar system for ordering and integrating multiple non-prescription medications. Many individuals take a large variety of vitamins, herbal supplements, herbs, oils, nutraceuticals, and other similar non-prescription medications. As with prescription medications, these drugs may also require variable dosing cycles/intervals, and the advantages that accrue from an integrated order packaged with all of the medications for a particular date and dosing interval are associated with non-prescription medications in substantially the same proportion that they are associated with prescription medications.

There is currently a lack of packaging solutions (either front-end or back-end) that allow a patient, doctor or caregiver to generate an integrated label for multiple medications. Thus, there is a need for a system capable of generating an integrated label, preferably a system capable of operating with any front-end pharmacy solution and any back-end automated filling robot.

The following description provides a convenient and efficient way for patients, pharmacists, and physicians to place orders for multiple tablets. The description also provides a system and method for integration of the multiple tablet orders, whereby patients may receive consolidated groups of tablets for administration at prescribed dosing intervals and prescribed quantities.

SUMMARY

A system for integrating and labeling a plurality of tablet orders is described. The system comprises a graphical user interface configured to receive a first input for a first plurality of tablets associated with a particular patient. The graphical user interface also receives a second input for a second plurality of tablets associated with the particular patient. The system further comprises a software module configured to compile the first input and the second input into an integrated order. The system also comprises an integrated label coupled to a package containing a first dose from the first plurality of tablets and a second dose from the second plurality of tablets. The integrated label indicates information about the first dose and the second dose.

In another embodiment, the system for integrating and verifying a plurality of tablet orders comprises a secondary container configured to contain a plurality of packages. The secondary container comprises a secondary label.

A method for integrating and labeling a plurality of tablet orders is also described. The method comprises receiving with a graphical user interface a first input for a first plurality of tablets associated with a particular patient. A second input for a second plurality of tablets associated with a particular patient is also received with the graphical user interface. The method further comprises compiling with a software module the first input and the second input into an integrated order. The method further comprises generating with the software module an integrated label to couple to a package containing a first dose from the first plurality of tablets and a second dose from the second plurality of tablets. The integrated label indicates information about the first dose and the second dose.

DRAWINGS

The present invention will be more fully understood by reference to the following drawings which are for illustrative, not limiting, purposes.

FIG. 10 shows an illustrative patient interface, including package selection options.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the methods may vary as to details, order of the actions, or other variations without departing from the illustrative methods disclosed herein.

The ordering system described herein may operate with any front-end pharmacy solution and any back-end automated filling robot. The goal is to consolidate prescription or other tablet orders by combining the orders and generating an output. This is done by putting all the orders into a database and then gathering information about each order and then combining this information with a photograph of each tablet that is also stored in the database. The consolidated order information with the associated written information and pictures of the tablets are combined into one booklet that is referred to as a patient information booklet.

Tablets as used herein may refer to any form of prescription or non-prescription medication in the form of caplets, pills, capsules, powders, liquids, gels, or suppositories, including vitamins, supplements, herbal formulations, or combinations thereof, intended to be ingested by or administered to a patient to improve the patient's health or well being.

The integrated label includes color pictures of the tablets. Additionally, the integrated label includes dosage periods (morning, noon, afternoon, evening) and information specific to the time frame (start date, no start date, week, month, 90-day period). The labeling may be in large alphanumeric text for improved legibility for the visually impaired.

Note, labeling may accommodate blind patient as shown and described in more detail in U.S. Provisional Application No. 61/245,912, filed Sep. 25, 2009, which is hereby incorporated by reference.

The integrated labeling is associated with the Patient Information Booklet (PIB). The PIB includes standardized language that corresponds to each medication. The PIB combines information associated with a plurality of medications into a single document. The PIB is included in the mail order package that is sent to the customer. The PIB is associated with the multi-prescription container and the integrated label, and the three are combined before being placed into a shipping container.

Figure 1:
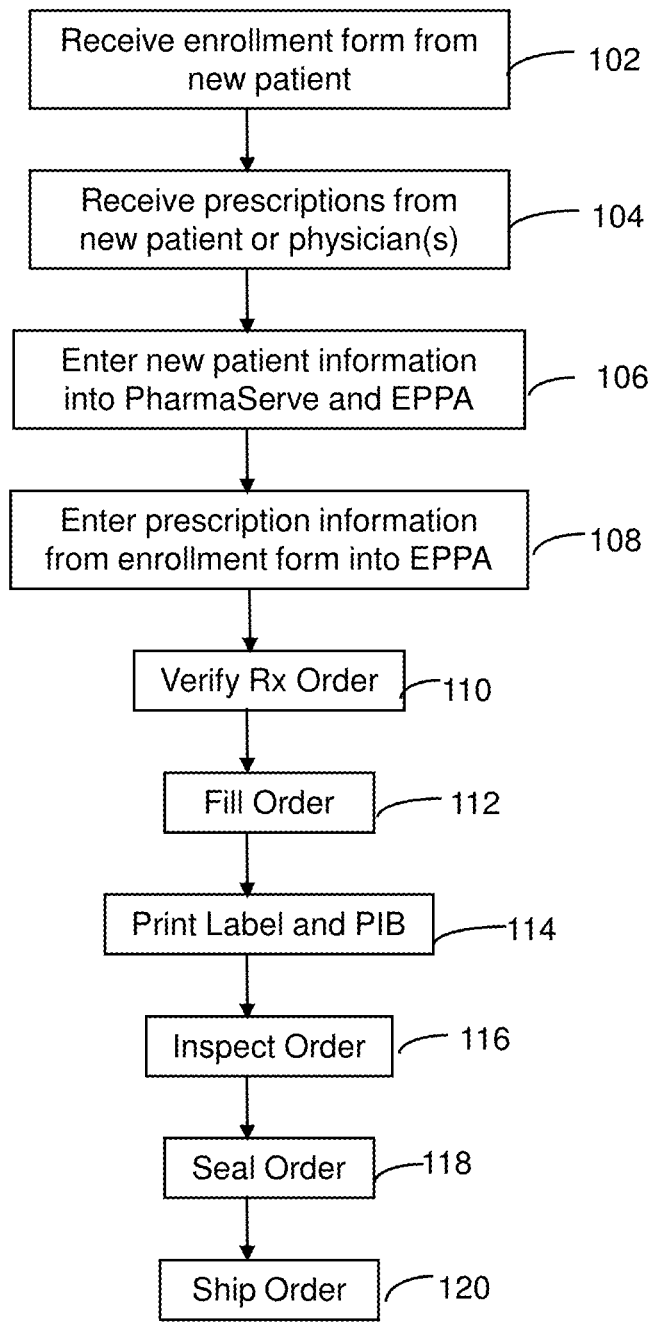
FIG. 1 shows an illustrative flowchart showing an overview of the process used to go from prescription entry to order shipment.

Referring to FIG. 1, there is shown an illustrative flowchart describing the overall process used to go from prescription entry to order shipment. At block 102, the enrollment form is received from a new patient. Proceeding to block 104, the enrollment form may be accompanied by the patient's written prescriptions, or the prescriptions may be faxed or otherwise delivered by the patient's physician(s). At block 106, the patient information is entered into the front-end system. In this illustrative embodiment, the front-end system is PharmaServe. Once the patient has been entered into PharmaServe, additional information including billing information and patient packaging preferences may be entered into Edge Prescription Processing Application (EPPA) at block 108. The method then proceeds to block 110, where the prescription order is verified.

Once the patient and prescription information have been entered into the front-end system and into EPPA, each prescription is now associated with a particular patient's individual regimen. The prescriptions are grouped and treated as one order within the EPPA system. This function is not available in PharmaServe or in other known front-end systems. The verified order is treated as a whole order from this point on in the process. Any additional prescriptions that the patient may require in the future may be added to the patient's order when prescriptions are next filled.

Moving on to block 112, the verified prescription order that is associated with a particular patient and corresponds to specific dates for administration is forwarded to production and filled. The illustrative interface, EPPA, communicates with the back-end (filling) system, allowing the prescriptions to be grouped as an order during filling. In one illustrative embodiment, the back-end system is Pac-Med.

The filling process uses automated techniques. During the filling process, the tablets that are associated with the prescription order may be loaded into compliance containers that are configured for use with the system and methods described herein, such as those described in U.S. patent application Ser. No. 11/923,321, filed Oct. 24, 2007, which is hereby incorporated by reference. Embodiments of compliance containers that are configured to be used with the system and methods herein are also described in more detail below.

The particular type of compliance container that is used during filling is chosen according to patient packaging preferences.

Referring now to block 114 of FIG. 1, the method proceeds to printing of the integrated label and the patient information booklet. The integrated labeling displays information relating to the patient. In some embodiments, a photograph of the patient may appear on the integrated labeling. Integrated labeling also displays detailed information about the tablets included in the prescription order. In some embodiments, color images of the tablets are included next to their names and descriptions. Further, integrated labeling contains drug precaution information corresponding to the tablets in the order. Integrated labeling may also include patient-specific or prescription order-specific information, such as details about interactions between two tablets in the order or interactions that the drug may have based on information that is specific to the patient, like age or the disease that is being treated. It is important to note that the steps of block 112 and 114 may also occur in reverse order, or simultaneously, without deviating from the system and methods described herein.

Also at block 114, the patient information booklet is printed. The patient information booklet is a consolidated booklet that displays information related to each tablet in the prescription order. The patient information booklet may display all, or a portion of, the information that may be included on the drug information insert that accompanies medications when they are dispensed in pill containers that hold just one type of tablet. The patient information booklet may also include more detailed information of the types described above in reference to integrated labeling, and it may contain other information related to the patient and/or the prescription order that may be useful to the patient or caregiver who uses the compliance packaging and patient information booklet.

Moving on to block 116, the filled order is inspected. The inspection process includes verifying that the tablets to be dispensed are properly associated with the particular patient and prescription order. The inspection process also includes inspection of the filled packages to ensure that the distribution of the tablets within the containers is consistent with the patient's dosage regimen. Further, the integrated labeling corresponding to a particular time period and specific dates for administration is associated with the strip of pouches or cups that contain the associated tablets. The integrated labeling associated with the order is also inspected and verified to be of legible print quality. Inspected strips are matched with the appropriate secondary container and the corresponding integrated labeling.

Moving on to block 118, the strips are sealed within the appropriate secondary container, and all secondary containers corresponding to a complete order are placed into a shipping container. Moving on to block 120, the shipping container with the prescription order within is forwarded to shipping for delivery to the patient.

Figure 2:
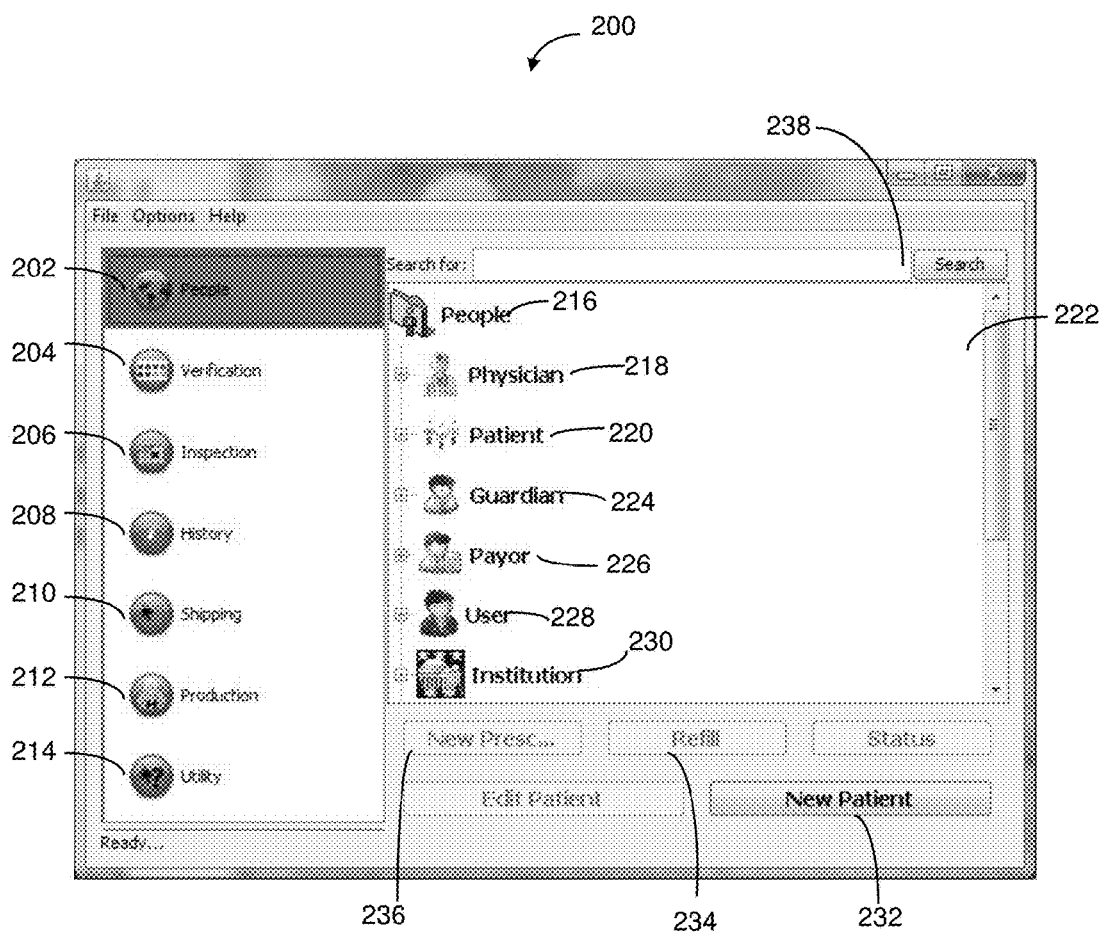
FIG. 2 shows a plan view of an illustrative EPPA GUI main screen.

Referring to FIG. 2, there is shown a plan view of an illustrative EPPA Graphical User Interface (GUI) main page 200. Starting on the left side of the illustrative GUI 200, there is shown a series of tabs 202-214. Each tab is associated with a particular set of tasks or type of information that needs to be interacted with. "People" tab 202 is highlighted in this illustrative image. Other illustrative tabs that are associated with steps in processing a patient prescription order include "Verification" tab 204, "Inspection" tab 206, "Shipping" tab 210, and "Production" tab 212. The illustrative "History" tab 208 allows a user of the GUI to pull up information related to the patient's history and the history of any previous associated prescription orders. The illustrative "Utility" tab 214 allows a user to manipulate EPPA settings and the like.

Since the people tab 202 is highlighted, "People" folder 216 is displayed at the top of the display area 222 to the right of the tabs 202-214 discussed above. The people folder 216 is shown in an expanded view, and subfolders physician 218, patient 220, guardian 224, payor 226, user 228, or institution 230 may be selected. These subfolders enable a user to obtain additional information about a person or entity of the type listed, or to enter such information. Below display area 222 is a series of buttons that include new patient button 232, refill button 234, and new prescription button 236. Search box 238 also enables a user to enter a search term in order to find or enter information.

Figure 3:
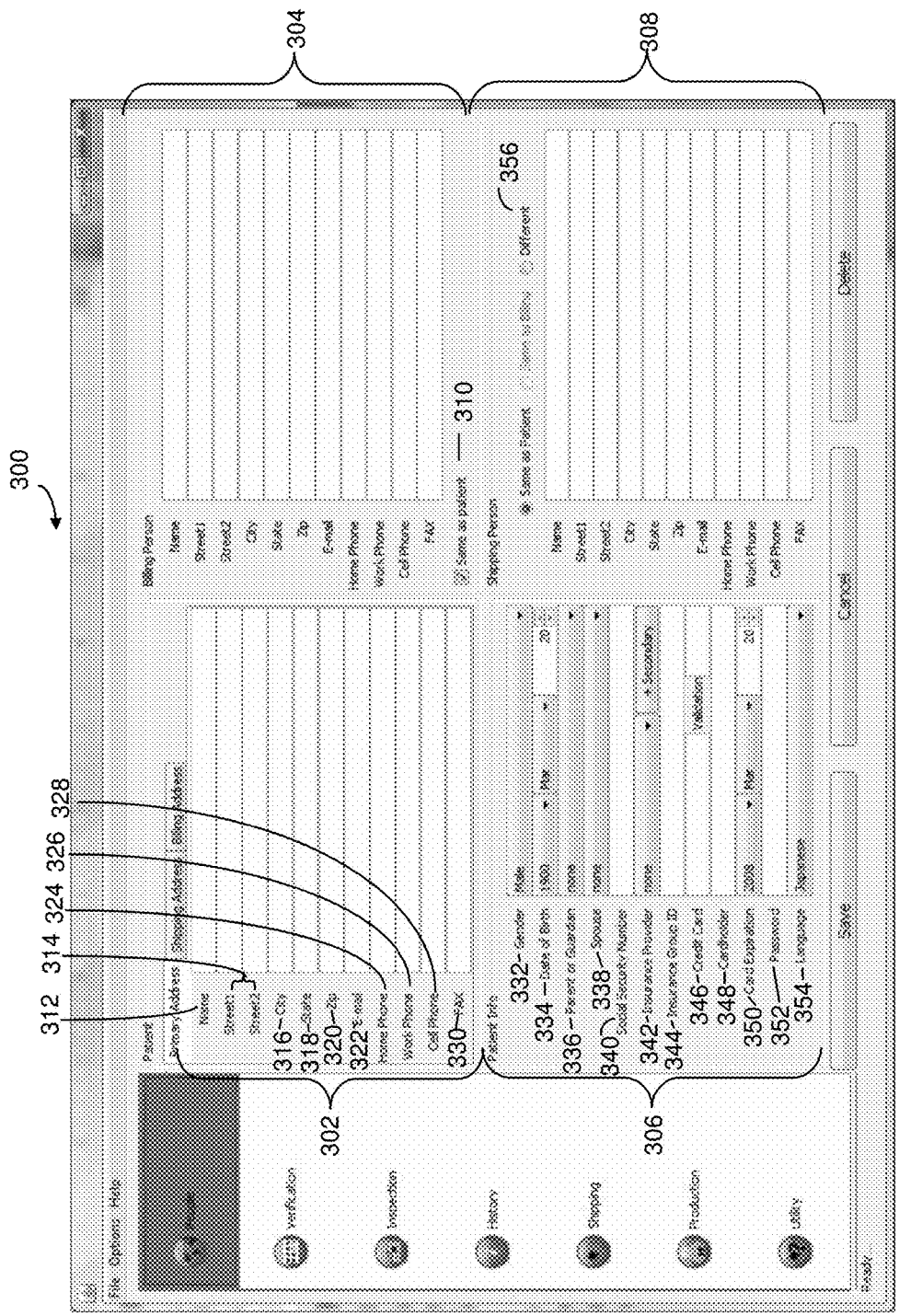
FIG. 3 shows a plan view of an illustrative EPPA GUI for patient information entry.

Referring to FIG. 3, there is shown a plan view of an illustrative EPPA GUI for patient information entry. The illustrative patient information entry GUI 300 is included under the highlighted people tab 202, as shown. The illustrative GUI 300 includes an area to enter or view information about the patient's address and contact information 302. Information corresponding to a patient's name 312, street 314, city 316, state 318, zip 320, email 322, home phone 324, work phone 326, cell phone 328, or fax number 330 may be entered. If an individual other than the patient is the contact person for billing, the check box 310 may be unchecked and billing address and billing contact information 304 may be entered or viewed.

Additional patient information 306 may be entered, including the patient's gender 332, date of birth 334, parent/guardian 336, spouse 338, Social Security number 340, insurance provider(s) 342, insurance group ID 344, credit card information 346, cardholder name 348, card expiration date 350, password 352, and language choice 354. If the shipping address and contact information 308 is different than both the patient information 302 and the billing contact information 304, then the choice "Different" may be clicked of the options 356, and the shipping information 308 may be entered.

Figure 4:
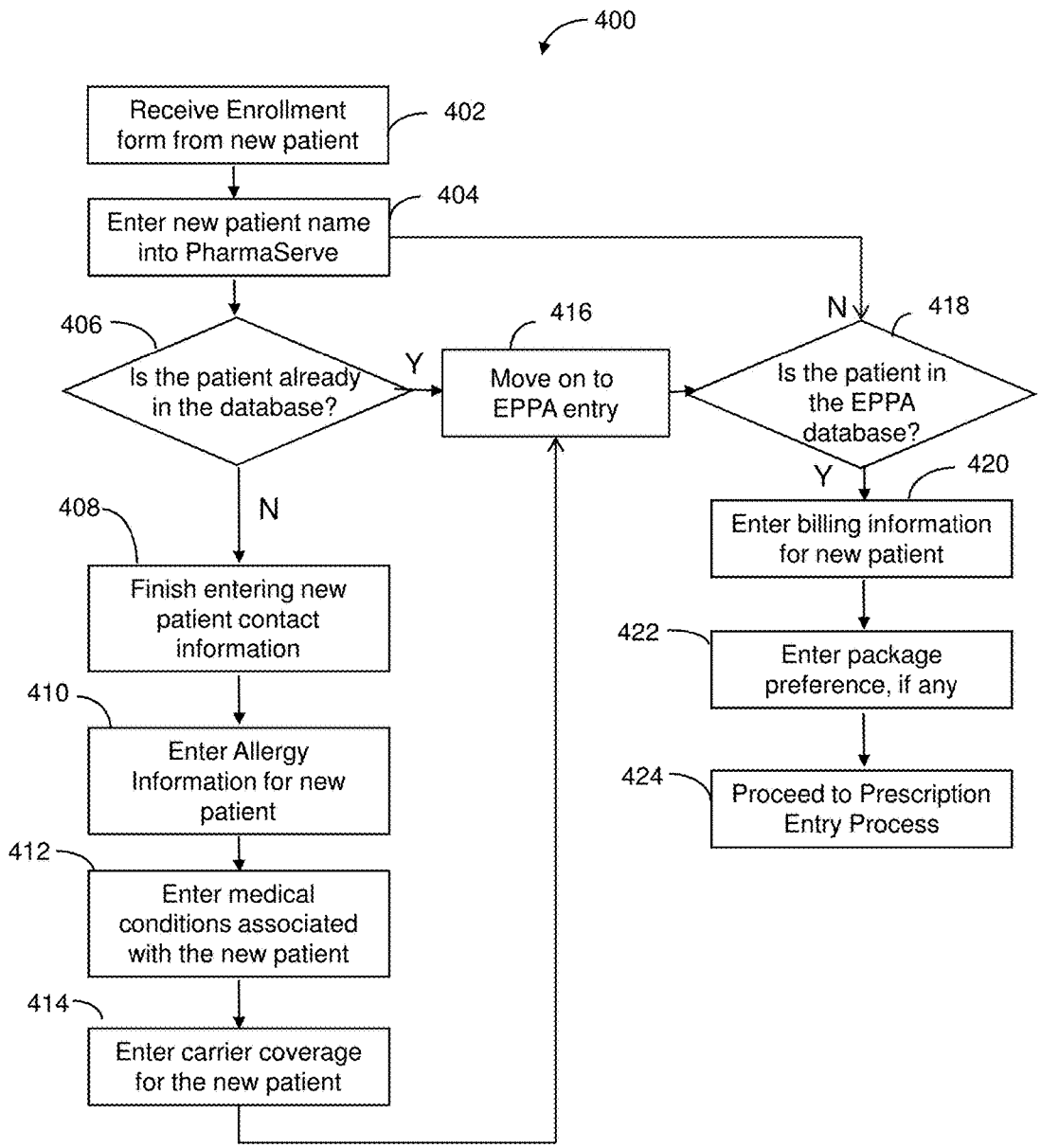
FIG. 4 shows an illustrative flow chart demonstrating the method of entering a new patient into the system.

Referring to FIG. 4, there is shown an illustrative flow chart depicting the process 400 for entering a new patient into the system. First, at block 402, the enrollment form is received from the patient. The enrollment form is typically accompanied by the new patient's written prescriptions, or by an instruction for the patient's physician(s) to be contacted to obtain the prescription information. Next, at block 404, the patient's name is entered into the database. In this illustrative embodiment, the patient name is entered into the illustrative front-end system, PharmaServe. The method then proceeds to decision diamond 406, where it is determined if the patient is already in the database. If the patient is in the database, the patient is not a new patient and the method proceeds to EPPA (Edge Prescription Processing Application) entry at block 416. If the patient is not in the database at decision diamond 406, the method proceeds to block 408, where the rest of the patient information is entered, possibly including patient information of the types described above for FIG. 3 EPPA patient entry. The method then proceeds to block 410, where any patient allergies are entered into the system. Proceeding to block 412, any patient medical conditions are entered, and moving on to block 414, the patient's detailed carrier coverage information is entered. The method then proceeds to block 416, where EPPA entry begins, and on to decision diamond 418, where it is determined if the patient is in the EPPA database list. If not, the method returns to block 404. If so, the method moves on to block 420, where patient billing information including credit card, driver license number and state is entered into a GUI similar to the one shown in FIG. 3. Patient notes that may describe anything related to the patient and/or the disease for which the patient is being treated and/or the prescription(s) that the patient is taking may also be entered. Moving to block 422, any patient packaging preferences are entered. Finally, the method proceeds to block 424, and the new prescription entry process begins (shown in more detail in FIG. 6).

Figure 5:
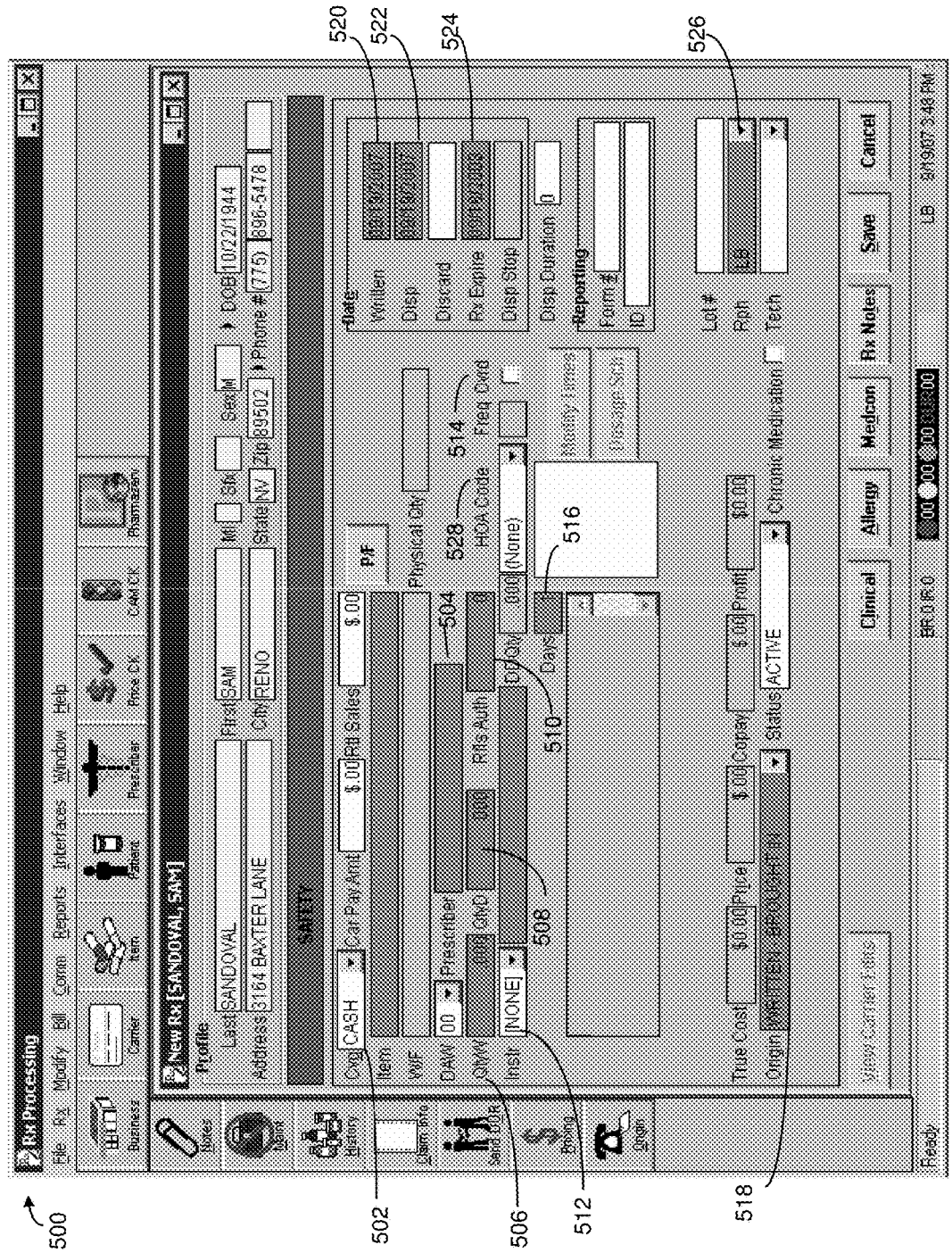
FIG. 5 shows an illustrative GUI for prescription order entry.

Referring now to FIG. 5, there is shown an illustrative GUI for entering additional prescription information. This information includes data about the insurance the covers the prescription, coverage (Cvg) information 502, prescriber information 504, refills authorized (Rfls Auth) 510, instructions (Inst) 512, frequency (Freq Ovrd) 514, the number of days supply 516, the origin of the tablets to be filled 518, the date the prescription was written 520, the date the prescription is being dispensed 522, the prescription expiration date 524, the pharmacist who is supervising the fill 526 and the hours of administration (HOA) information 528.

Figure 6:
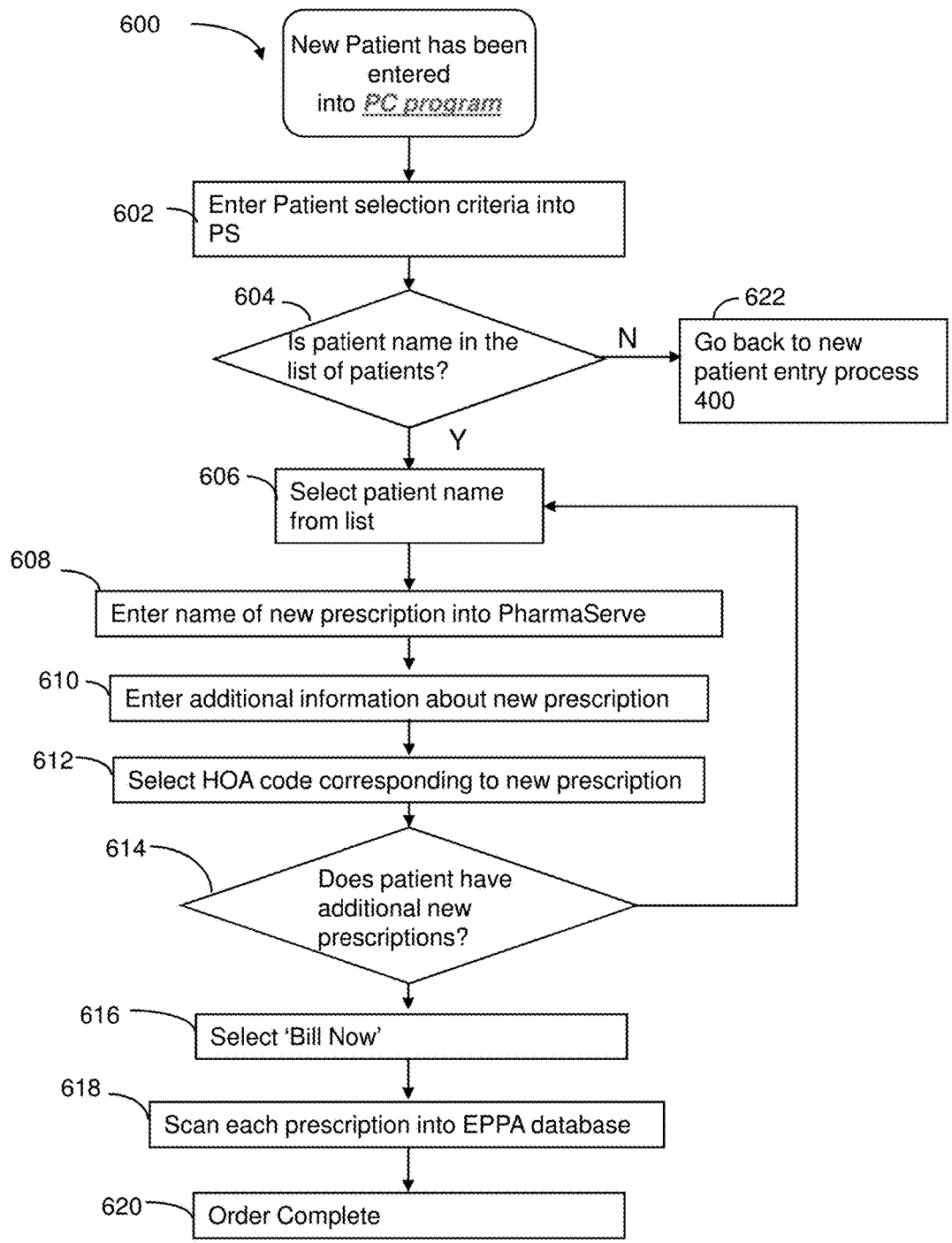
FIG. 6 shows an illustrative flow chart depicting the process A00 for entering a new prescription order into the system.

Referring now to FIG. 6, there is shown an illustrative flow chart depicting the process 600 for entering a new prescription order into the system. At block 602 of the method 600, patient selection criteria are entered into PharmaServe. Patient selection criteria may include patient last name, patient phone number, or other identifying information. The method then proceeds to decision diamond 604, where it is determined if the patient name is in the list of patients. If the name is not in the list of patients, the method proceeds to block 622, where method 400 (described in FIG. 4) is performed. If the patient name is found in the list of patients, the method proceeds to block 606, where the patient name is selected from the list. At block 608, the name of a new prescription associated with the patient is entered.

The method then proceeds to block 610, where additional information relating to the prescription is entered. This information is entered into an illustrative GUI similar to the one presented in FIG. 5. This information may include coverage (Cvg) information 502, prescriber information 504, refills authorized (Rfls Auth) 510, instructions (Inst) 512, frequency 514, the number of days supply (Days (supply)) 516, the origin of the tablets to be filled 518, the date the prescription was written 520, the date the prescription is being dispensed 522, the prescription expiration date 524, and the pharmacist who is supervising the fill 526.

Referring back to FIG. 6, the method proceeds to block 612, where the HOA code 528 (shown in FIG. 5) corresponding to the time(s) and frequency that the medication should be taken is entered. The HOA code enables an individual prescription to be integrated into an individualized regimen and associated with the proper medicament container for eventual administration.

The method then proceeds to decision diamond 614. If the patient has additional new prescriptions to be added, the method returns to block 606. If all new prescriptions have been added to the system, the method proceeds to 616, where the illustrative "Bill Now" command is entered, which ends the data entry process. The method then proceeds to block 618, where the handwritten prescriptions corresponding to each prescription to be dispensed are scanned into the system. Finally, the method proceeds to block 620, where the order is complete.

Figure 7:
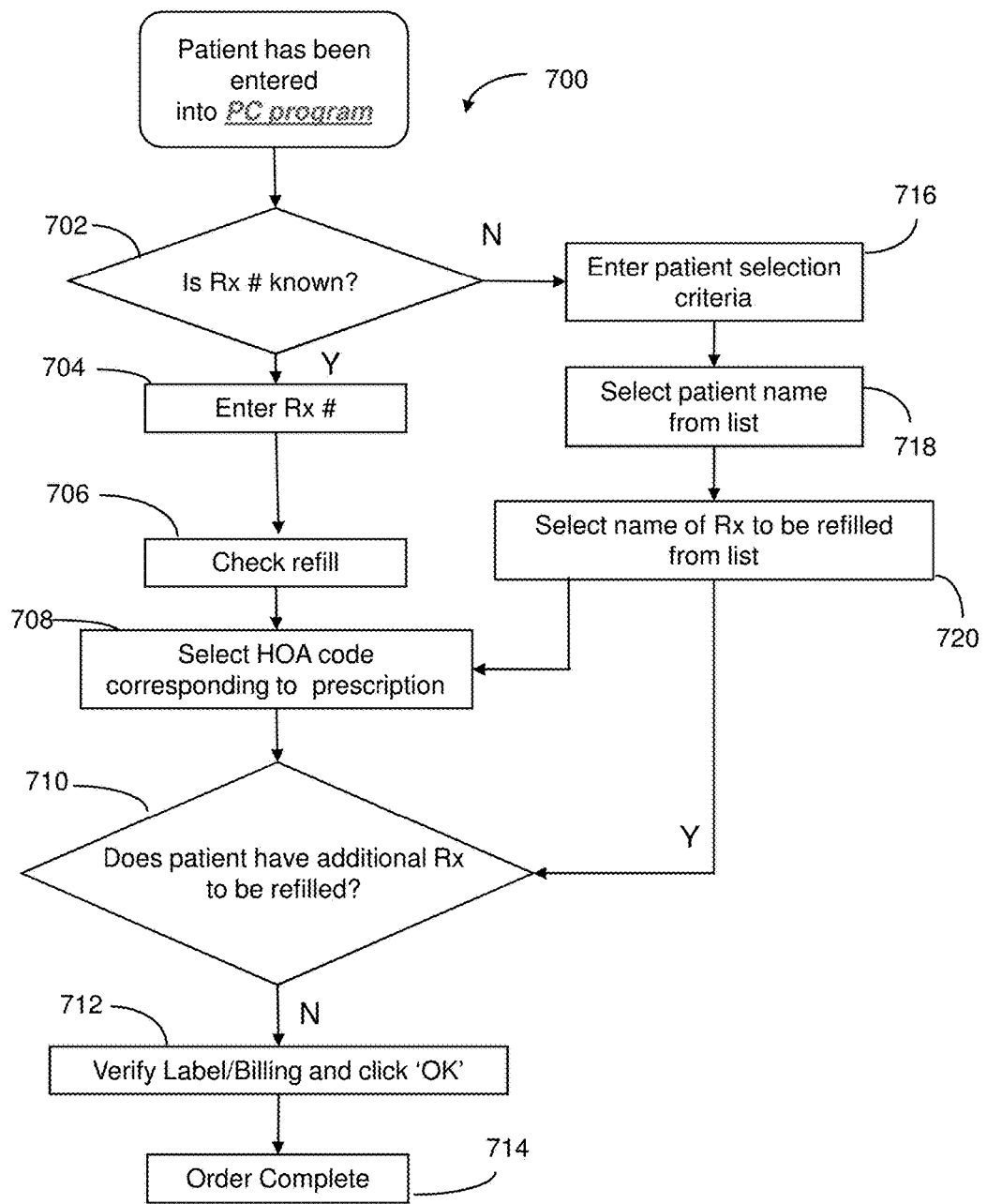
FIG. 7 shows a flow chart of an illustrative process 700 for entering a refill Prescription.

Referring now to FIG. 7, an illustrative process 700 for entering a refill prescription is shown. At decision diamond 702, the method selects whether the prescription is known. If not, the method proceeds to block 716, where at least one patient selection criterion is entered, and on to block 718, where the patient name is selected from a list. The method then proceeds to block 720, where the prescription to be refilled is selected from a list associated with the patient.

Alternatively, if the prescription number is known at decision diamond 702, the method proceeds to block 704, where the prescription number is entered. In either case, the method proceeds from either block 704 or 720 to block 706, where the option "Refill" is selected. The method then proceeds to block 708, where the HOA code associated with the particular patient and particular prescription is entered.

The method then proceeds to decision diamond 710, where it is determined if the patient has additional prescriptions to be refilled. If the patient has additional prescriptions to be refilled, the method proceeds to block 720, where the next Prescription to be refilled is selected. The method then moves on to block 706, where the 'Refill' option is selected; next, the method proceeds to block 708, where the HOA code associated with the particular patient and particular prescription is entered. The method then returns to block 710, and it is again determined if there are additional prescription to refill.

When there are no prescriptions left to refill, the method proceeds from decision diamond 710 to block 712, where the label and billing information associated with the prescription order is verified. The method then proceeds to block 714 where the order is complete.

Figure 8:
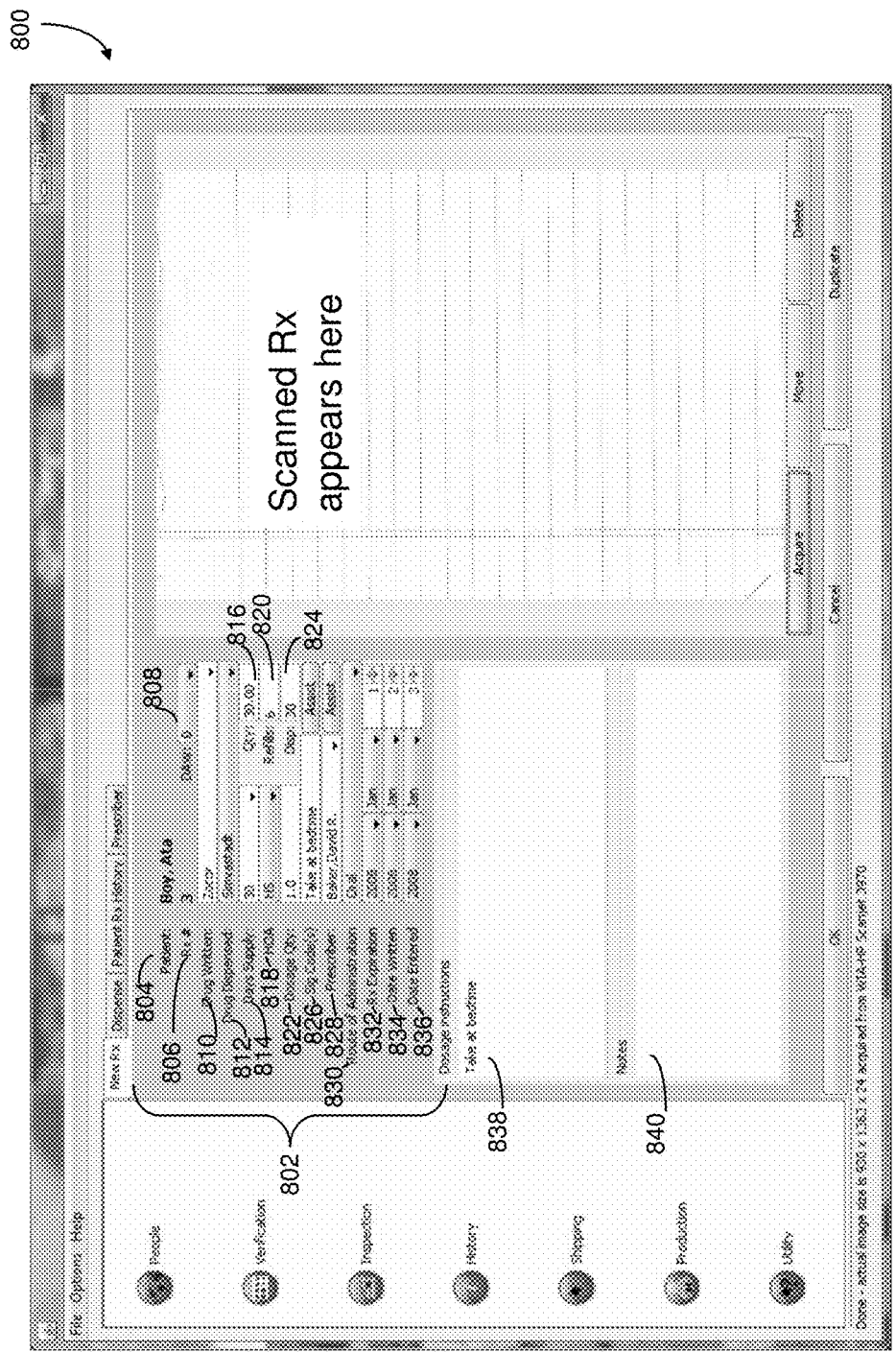
FIG. 8 shows an illustrative process EPPA GUI for entering a new prescription, including the scanned handwritten prescription.

Referring now to FIG. 8, there is shown an illustrative prescription display comparison EPPA GUI 800. The illustrative GUI 800 is configured to display an image of the scanned handwritten prescription for comparison and/or data entry. Information about a specific prescription in a prescription order may be entered into this illustrative GUI 800. The scanned prescription 802 appears in the display window at the right of the GUI 800. Information including patient name 804, prescription number 806, the name of the drug written on the prescription 810, the name of the dispensed drug 812, the number of days supply 814, the quantity of tablets 816 that corresponds to the number of days supply, the HOA code 818, number of remaining refills 820, dosage quantity 822, the quantity of tablets 824 that corresponds to the dosage quantity, the sig code(s) 826, the prescriber name 828, route of administration 830, the prescription expiration date 832, the date written 834, and the date entered 836 may be viewed or entered into GUI 800. Additionally, dosage instructions 838 and notes 840 may be viewed or entered into GUI 800. In some embodiments, a user is able to make notations on the electronic image of the prescription as a removable layer such that the original prescription image can be viewed in the GUI with or without the notations.

Figure 9A:
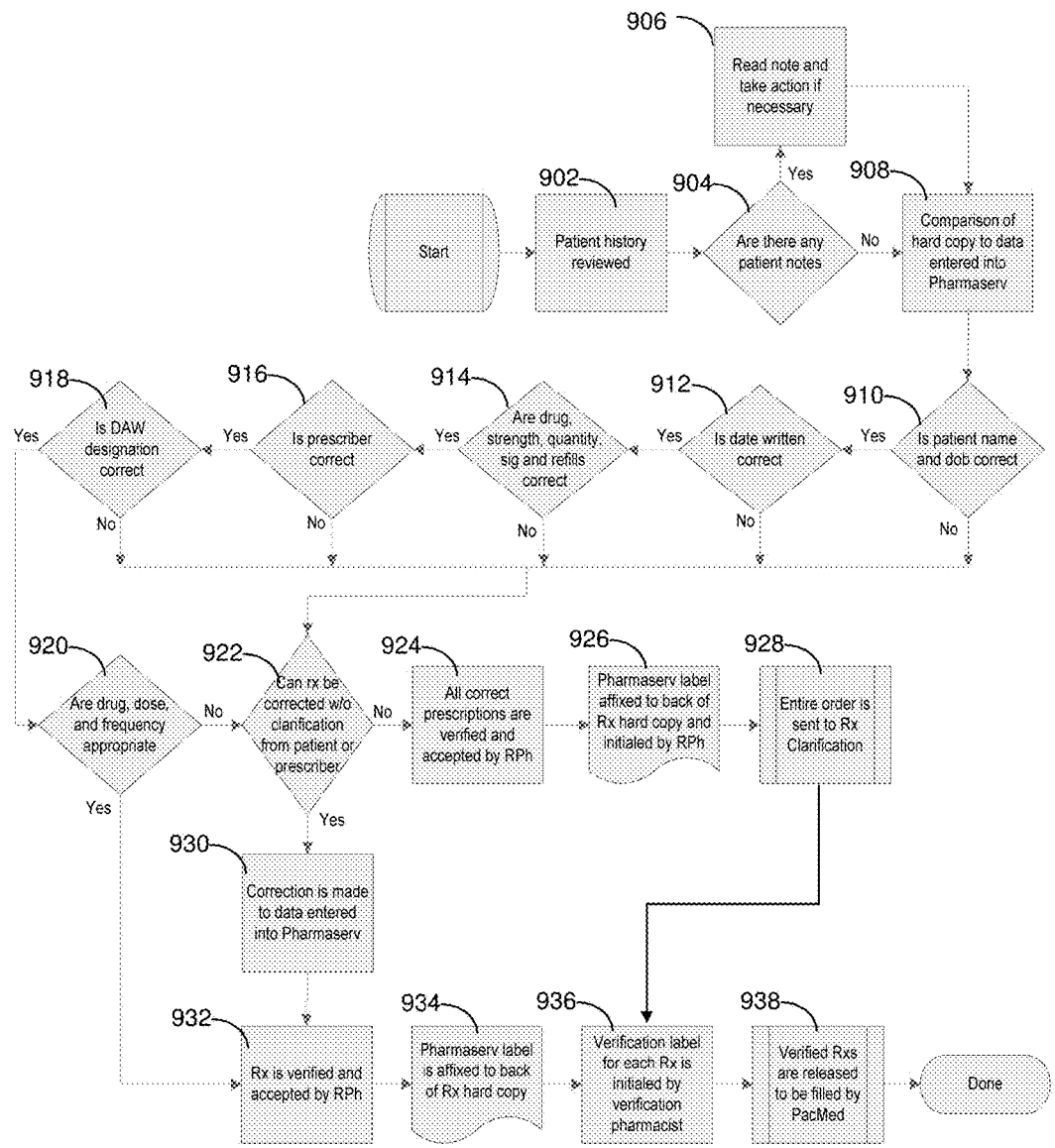
FIG. 9A illustrates an embodiment of the prescription input verification process.

With respect to FIG. 9A, an overview of the prescription order verification process is shown. The verification process authenticates the accuracy of each prescription input. First, at block 902, a patient's history is reviewed. The patient's history is compared to the plurality of prescription inputs to ensure therapeutic appropriateness.

As used herein, therapeutic appropriateness refers generally to the suitability of an integrated prescription order (or, the totality of prescription inputs) for a particular patient. Therapeutic appropriateness is determined by a number of factors. For instance, one important factor is whether a patient has a history of overuse or abuse of one or more drugs in the integrated order. Additionally, a patient's history of compliance (e.g., underuse or irregular use) as well as a reported effectiveness/ineffectiveness may be considered. An integrated order may be further evaluated to ensure that no medications in the order contain any substance known to cause an allergic reaction in the patient. A patient's medical diagnosis (e.g., recovering, terminally ill, advanced, intermediate, and early stages) may also aid in determining the therapeutic appropriateness of an integrated order. Therapeutic appropriateness may also depend on the likelihood of interaction—i.e., between several medications in an integrated order and/or between medications in the order and medications a patient is taking, or has recently taken, not associated with the order. Finally, the determination may include an evaluation of an integrated order to ensure that there are no therapeutic duplications or contraindications.

After it has been determined that an integrated prescription order is therapeutically appropriate, at block 904 it is determined whether there are any notes associated with a particular patient. These notes may describe changes to a patient regimen as well as any other pertinent information. If notes exist, the method proceeds to block 906, where the notes are processed or read and any necessary action referred to in the notes is taken. Thereafter, the process continues to block 908. If, on the other hand, there are no patient notes, the process simply advances to block 908. Beginning with block 908, the original handwritten prescription orders, or scanned images thereof, are compared to their associated prescription inputs to ensure that the prescription inputs are correct. More particularly, for each prescription input, the patient's name and date of birth are verified (block 910), the date that the prescription was written is verified (block 912), the drug strength, drug quantity, number of refills, and presence of a physician's signature are verified (block 914), the prescriber information is verified (block 916), the dispense as written (DAW) designation is verified (block 918), and, finally, the drug, the dosage, and the dosage frequency are verified (block 920).

If a prescription input can be verified at all of blocks 910-920, the prescription input is verified and approved by a pharmacist at block 932, a label is affixed to the back of the prescription order at 934, a verification label is initialed by a pharmacist at 936, and the prescription input is released to be filled by a filling machine at 938.

If a prescription input cannot be verified at one or more of blocks 910-920, an attempt may be made to correct the invalid prescription input at diamond 922. Corrections are made by re-entering all of the invalid portion of the prescription input. If possible, the invalid prescription input is corrected at block 930, whereafter the prescription input is verified and approved by a pharmacist at 932, a label is affixed to the back of the prescription order at step 934, a verification label is initialed by the verifying pharmacist at block 936, and the approved prescription input is released to be filled by a filling machine at block 938.

If, however, a prescription input cannot be corrected as specified above, clarification by the patient or prescriber may be required. If clarification is required, the method proceeds to block 924, where all correct prescription inputs (i.e., those that do not require clarification) are verified by a qualified pharmacist. Thereafter, a label is affixed to the back of each associated prescription order and initialed by a pharmacist. Prescriptions may be clarified by contacting a patient or physician via email, facsimile, telephone, or any other such means; and, the inquiry may be made for additional or corrected information. Once the order is clarified, the method proceeds to block 936, where the verification label for each prescription is initialed by a pharmacist. Finally, the clarified (and verified) order is released for filling at block 938.

Referring to FIGS. 9B through 9E, an embodiment of a verification GUI is displayed. The verification GUI comprises a software module and is configured, in broad terms, to display one or more prescription inputs for review by a pharmacist or, potentially, by a software module configured to verify and approve prescription inputs. As described above with reference to FIG. 9A, a pharmacist may utilize the verification GUI as a means for comparing each prescription input to a hardcopy or scanned image of its associated prescription order.

Figure 9B:
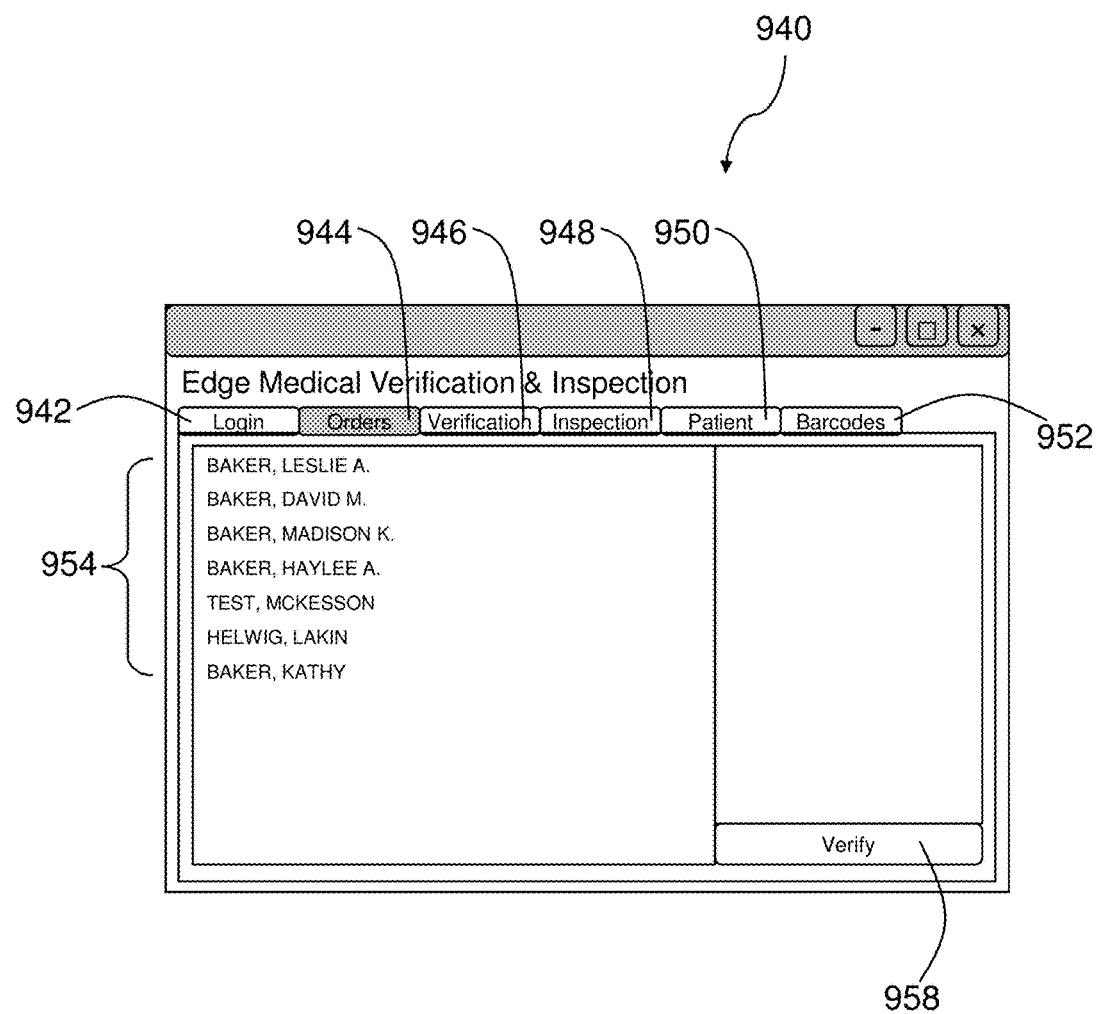
FIG. 9B shows a first view of a graphical user interface configured to facilitate patient and order selection.
Figure 9C:
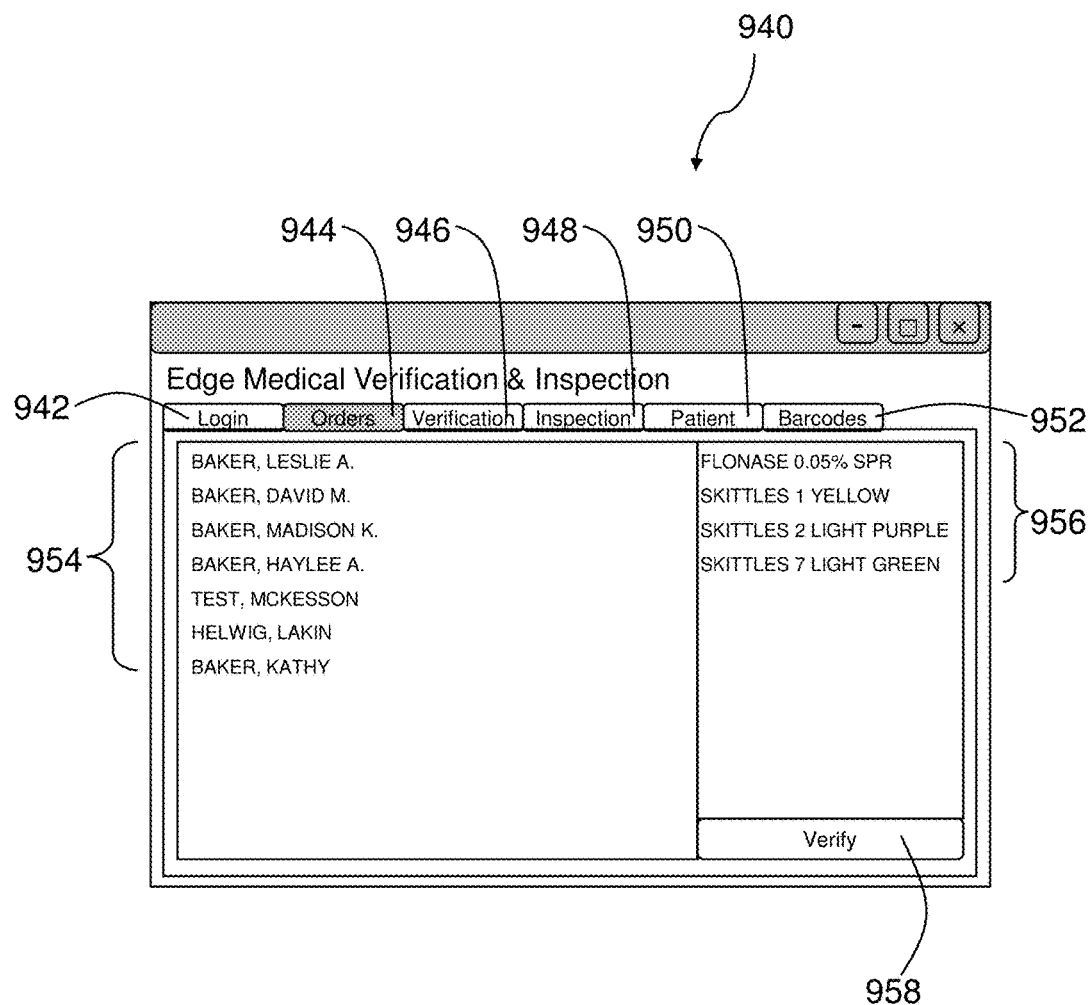
FIG. 9C shows a first view of a graphical user interface configured to facilitate patient and order selection.
Figure 9D:
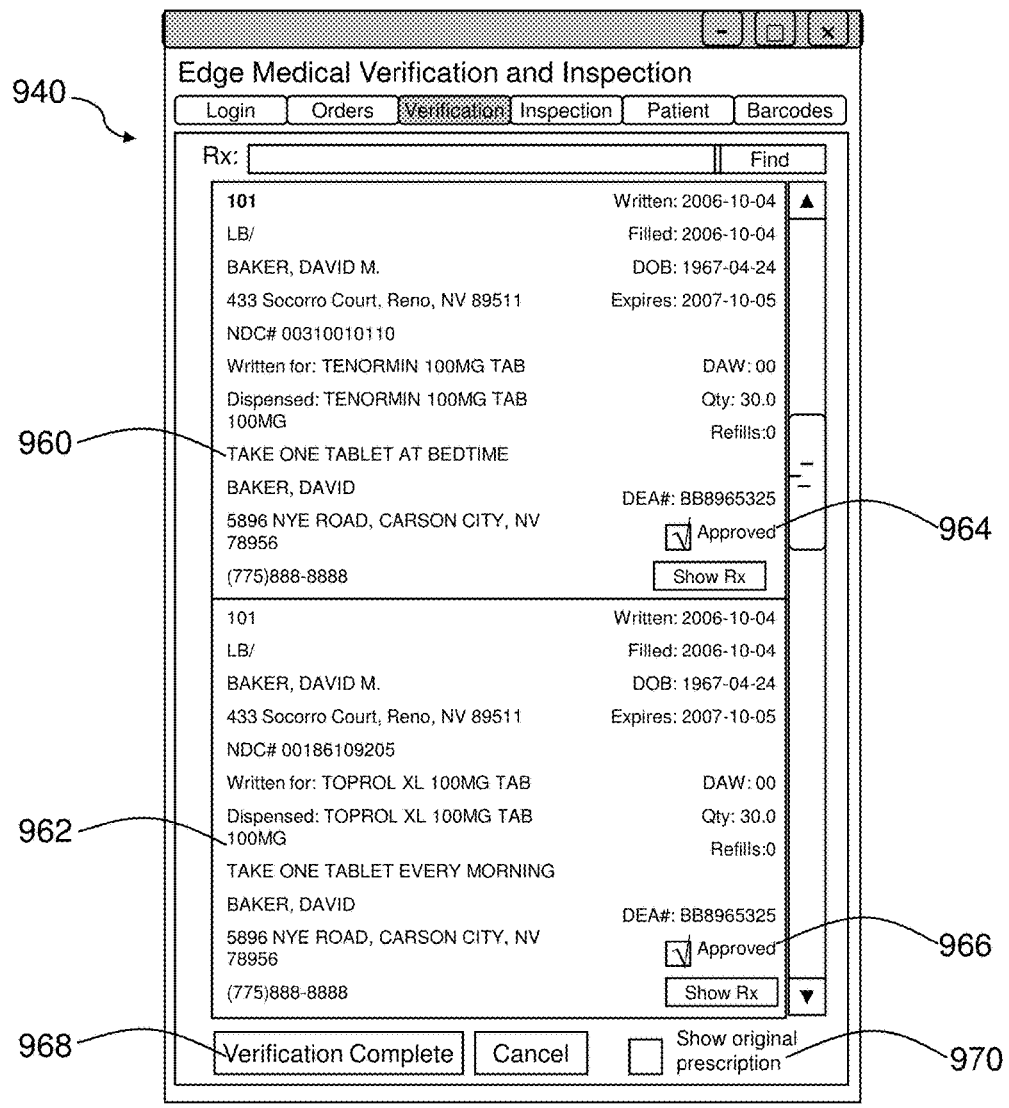
FIG. 9D shows a first view of a graphical user interface configured to facilitate prescription input verification.

To that end, referring now to FIG. 9B, the verification GUI first comprises a patient/order selection interface 940. The patient/order selection interface 940 comprises a plurality of tabs for performing various operations. More particularly, the interface 940 comprises a login tab 942, an orders tab 944, a verification tab 946, an inspection tab 948, a patient tab 950, and a barcodes tab 952. However, depending upon a user's (e.g., a pharmacist's) capability profile fewer than all of the tabs may be displayed on successful login. After the orders tab 944 is invoked, the software groups all outstanding prescriptions and displays a list 954 of all patients with outstanding orders. Referring to FIG. 9C, selecting a patient from the list 954 of patients with outstanding orders populates the right hand side of the patient/order selection interface 940 with a list of all of the unverified and outstanding prescription orders 956 for the selected patient. Double clicking a patient name or selecting the Verify button 958 at the bottom right hand corner of the interface 940 populates and invokes the verification tab 946.

Figure 9E:
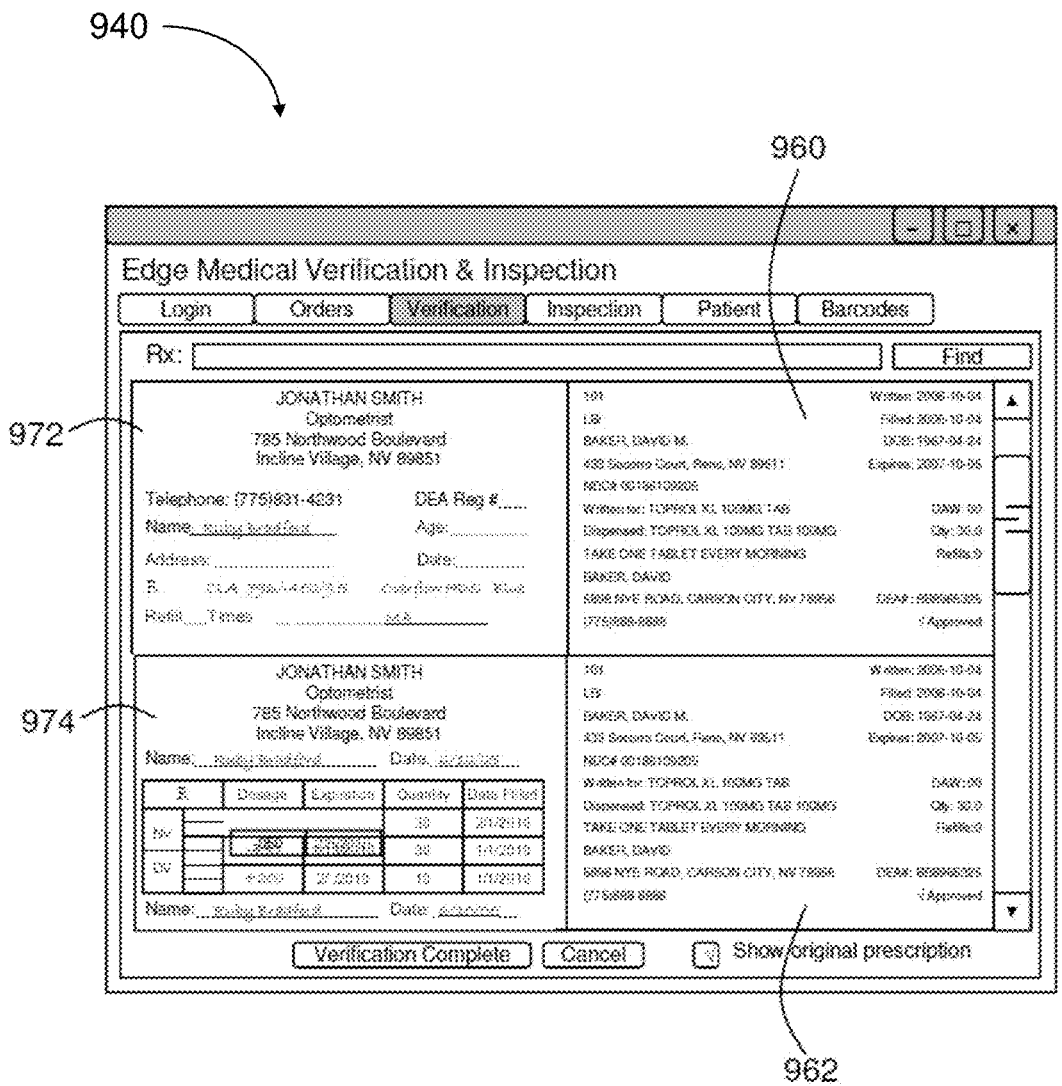
FIG. 9E shows a second view of a graphical user interface configured to facilitate prescription input verification.

Under the verification tab 946 the software displays all of the unverified prescription inputs. Here, there are two example prescription inputs, 960 and 962. These are the prescription inputs that require verification and approval, as described above with reference to FIG. 9. More particularly, the verification GUI displays the information associated with each prescription input, whereby a pharmacist may compare the information displayed by the GUI to the information on, either, a hardcopy prescription order corresponding to the prescription input she is viewing, or a scanned image of the prescription order corresponding to the prescription input she is viewing. A checkbox 970 labeled "Show original prescription" permits the user to toggle between a first view (FIG. 9D) and a second view (FIG. 9E). Referring to FIG. 9E, the second view juxtaposes each prescription input 960 and 962 with a scanned image of the associated prescription order 972 and 974, respectively.

After verifying all the information in a particular prescription input, the pharmacist may approve the prescription input by checking a box, 964 and 966, labeled "Approved" associated with the particular prescription input, 960 and 962 respectively. Alternatively, a pharmacist may determine that a prescription input is inconsistent with its associated prescription order, in which case the pharmacist may choose to leave the Approved box associated with the invalid prescription input unchecked.

The pharmacist may indicate that verification has been performed by entering an input into the GUI, for example, by activating a "Verification Complete" button 968 after she has reviewed all of the prescription inputs. Other means for entering an input using a GUI, such as ticking a checkbox, entering a note in a data field, or entering a signature on a touchscreen interface, may be used in the GUI to allow the pharmacist to indicate that a verification has been performed. Selecting the Verification Complete button 968 causes each of the prescription inputs associated with a patient and displayed in the Verification tab 946 to be grouped as an integrated order and assigned a unique ID number. Further, the approved prescription inputs are no longer shown under the Verification tab 946, nor is the selected patient displayed under the Orders tab 944, provided of course that the pharmacist approved all outstanding prescription inputs associated with the patient.

The patient compliant medicament dispensing containers described herein are available in many different styles, allowing patients to make decisions about the type of medicament packaging that will best suit their needs. Patient-selectable packaging for multiple medication compliance regimens allows a patient to choose a medicament container system on the basis of several factors, including ease of opening, childproofing features, number of tablets to be consumed daily, and desired dosage grouping (7-day or 30-day).

Many younger individuals take only a few prescription medications. Most of these patients are able to easily open any of the many types of packaging available. A primary concern for this type of patient may be portability and sturdy construction of the packaging. The compliance aspect may be very simple—the package may just make the medications more readily portable than needing to take several bottles of pills around AND having to remember whether one took them that day or not. Further, this type of patient may travel often, and may desire that medications are dispensed in smaller dosage groupings, such as a 7-day grouping, to avoid having to carry around medications for an entire month when only travelling for a few days.

Patients with small children may find it is important that the packaging is child-proof. The compliance aspect will also help ensure parents that their medications are safe from tiny hands, since missing medication would be easy to detect.

On the other end of the spectrum, a patient who possesses limited manual dexterity may need a container system that is easy to open or may require assistance to take medications. Patients who consume several tablets at frequent intervals throughout the day or having many prescriptions to manage may benefit from compliance packaging indicating when tablets have been consumed. For a patient living in an assisted living facility or utilizing a caregiver, a compliance container system facilitating ease of distinguishing one patient's medications from another's may be preferred.

Figure 10:
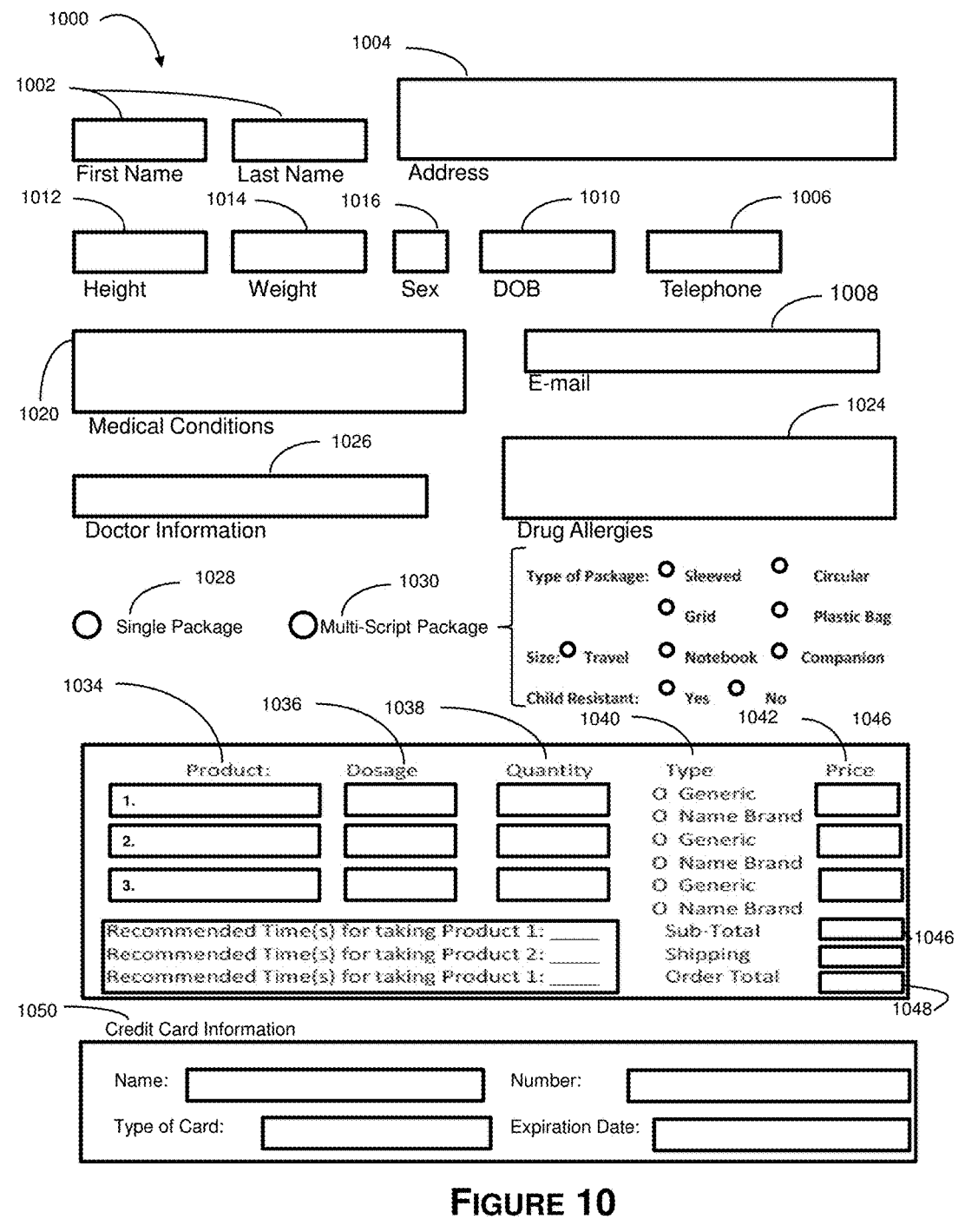

FIG. 10 shows an illustrative patient interface, including package selection options. The illustrative GUI 1000 embodiment is configured to receive a prescription order, a direct order, or any such order related to medications, vitamins, supplements, herbs, oils, or any such substance that is associated with a particular patient. The illustrative GUI 1000 includes fields for the name of the patient 1002 and the patient's address 1004. Additional information about the individual placing the order may also be requested, such as the individual's telephone number 1006 and e-mail address 1008. Information about the patient such as date of birth 1010, height 1012, weight 1014, and sex 1016 can also provided to the illustrative GUI 100. The user can input information about the patient's medical conditions 1020, information about the patient's doctor 1022, allergies 1024, and current medications 1026 being taken by the patient.

Furthermore, the user may select specific ordering options such as the type of packaging to be used for the medication. For example, a plurality of single packages 1028 may be requested for multiple medications. Also, a multiple prescription package 1030 or "multi-script" package may be requested. The multiple prescription package may include a variety of user selectable options such as type of package, size of package, and child resistant packaging. The type of package may include a sleeved package or a spiral package as described below. Alternatively, the packaging may employ other packaging techniques such as grid packaging or the use of plastic bags.

Data fields are also provided for identifying the requested medications 1032 that include a description of the product 1034, the dosage 1036, the quantity 1038, and the type of drug 1040. The type of drug 1040 may include information about whether the drug is generic or name brand. If the product is available, the on-line ordering system may then provide a price 1042 for the product. A sub-total 1044 is then provided, and shipping costs 1046 are identified. A final order total 1048 is then presented to the user. The patient may then provide a card 1050 such as a credit card, a debit card or any other such information for conducting an on-line transaction. The name, the card number, the type of card and the expiration date of the card are requested in the illustrative embodiment.

Figure 11:
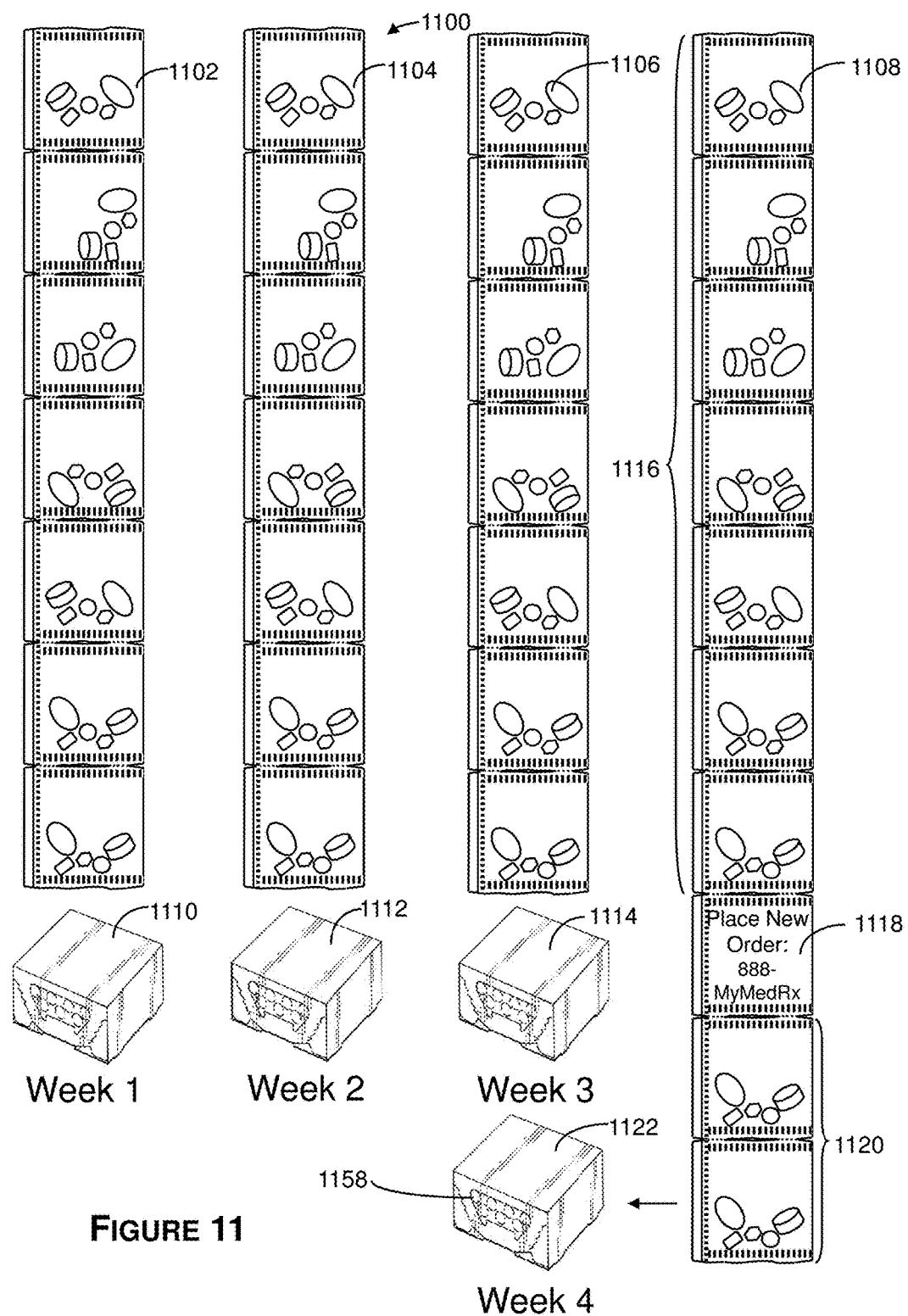
FIG. 11 shows an illustrative grouping for a 30-day tablet regimen for one illustrative type of compliance packaging.

Referring to FIG. 11 there is shown a 30-day tablet regimen for the patient medication management system that uses the seven-day box. A patient medication management system 1100 provides a compliance packaging solution. The patient medication management system 1100 described herein provides a compliance package because, firstly, an action is required by the patient or caregiver that requires identifying the appropriate dosage period, e.g. morning, and selecting the appropriate pouch. Secondly, the patient opens the appropriate pouch and consumes the medication. Thirdly, the patient or caregiver records the consumption of the medication by removing or pressing the circular cuts.

The patient medication management system 1100 comprises a plurality of sealed pouches that are grouped into four separate strips 1102, 1104, 1106 and 1108. The first strip 1102 is a seven day strip that covers the illustrative dates of 9/22/07 through 9/28/07 and the illustrative dosing period is the "morning." In the illustrative embodiment, the dosage period is selected from the group of dosage period intervals consisting of a morning dosage interval, a noon dosage interval, an evening dosage interval, or a bedtime dosage interval.

The first strip 1102 is placed into the illustrative folded box 1110 that has the tablets corresponding to the first week of the 30-day regimen. The second strip 1104 is a seven day strip that covers the illustrative dates of 9/29/07 through 10/05/07. The dosing period remains the same, i.e. morning. The second strip 1104 is associated with folded box 1112 that houses the tablets corresponding to the second week of the 30-day regimen. The third strip 1106 is a seven day strip that covers the illustrative dates of 10/06/07 through 10/12/07 and, again, the dosing period is the morning. The third strip 1106 is associated with folded box 1114 that corresponds to the third week of the 30-day regimen.

The fourth strip 1108 includes a seven day grouping of pouches 1116 that covers the illustrative dates of 10/13/07 through 10/19/07; the dosing period remains the same, i.e. morning. Additionally, an empty pouch 1118 is included with the fourth strip 1108 that provides a reminder to place another order and an illustrative 800 number to assist in placing the refill order. Furthermore, a two day grouping of pouches 1120 covers the illustrative dates of 10/20/07 through 10/21/07. The fourth strip 1108 is associated with folded box 322 that houses the tablets corresponding to the fourth week of the 30-day regimen. Thus, the fourth strip 1108 includes nine pouches that complete the 30-day regimen.

Each of the strips 1102, 1104, 1106 and 1108 are placed in the corresponding folded box 1110, 1112, 1114 and 1122, respectively. Each folded box or "primary container" is configured to receive at least seven pouches. Note, the terms folded box, assembled box, and "primary container" are used interchangeably though out this patent. Thus, each primary container is configured to receive at least seven pouches that correspond to the particular dosage period and the illustrative primary container is labeled with the dosage period corresponding to the medications. Additionally, each primary container may be labeled with the patient name and dosage period as described above.

Each folded box or primary container comprises a plurality of daily indicators corresponding to a seven-day period that are disposed on the primary container. The daily indicators provide a means for recording that the medications in the pouch have been taken. An illustrative embodiment of the daily indicators has been provided above that describes a plurality of circular cuts 1158 on the folded box. Each of the daily indicators is configured to indicate that the medications in the pouch have been taken, thereby providing a means for compliance packaging.

In the illustrative 30-day regimen, the sealed pouches associated with strips 1102, 1104, 1106 and 1108 include sealed pouches with a plurality of different tablets that correspond to different medications and/or vitamins. The different medications are associated with at least one prescription and each tablet includes an appropriate dosage consistent with the prescription. Each of the sealed pouches is labeled to show the medications in the pouch and labeled with a particular dosage period that includes at least one daily interval for consuming the medications in the pouch.

Figure 12:
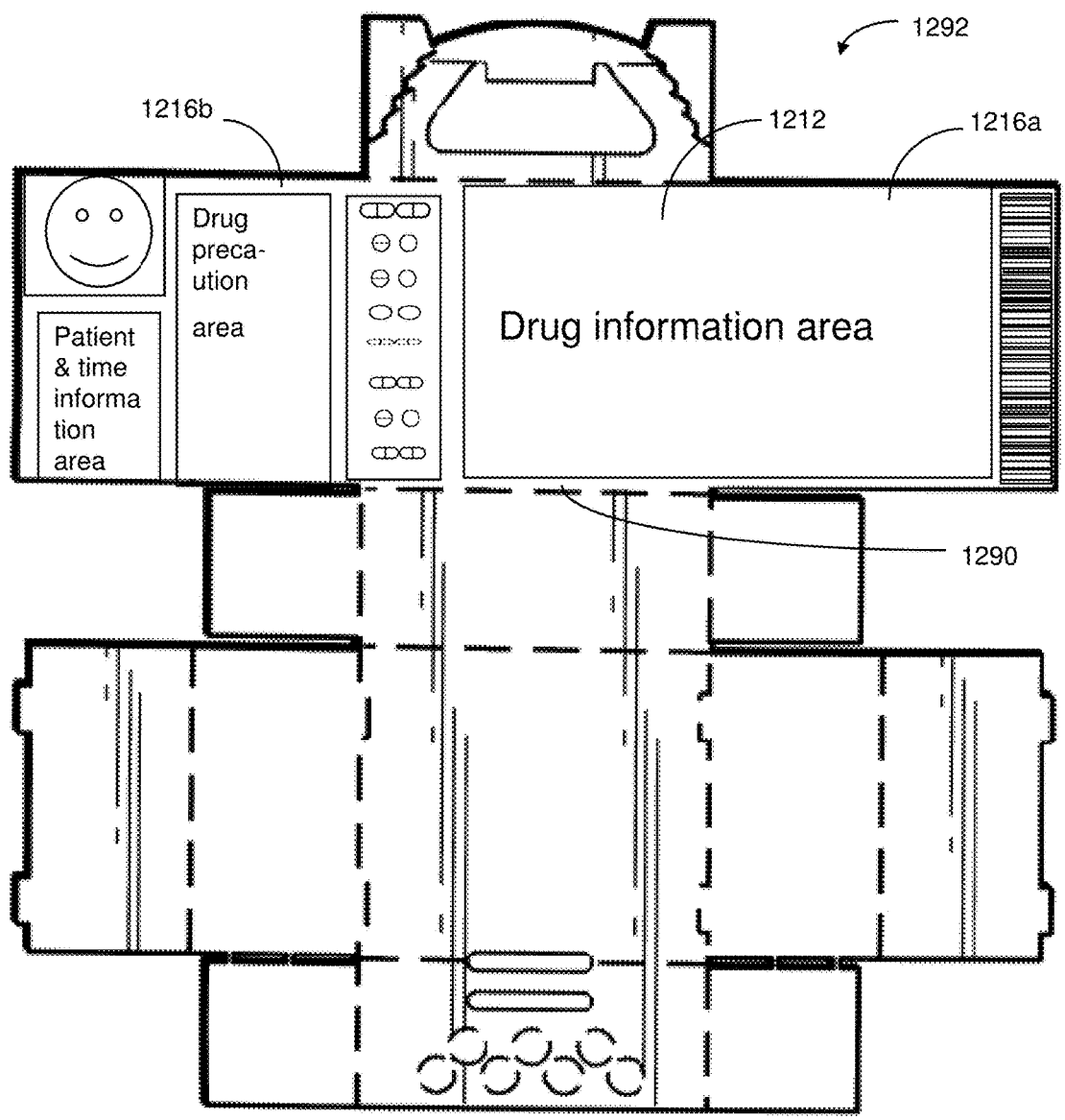
FIG. 12 shows a label area on a pre-assembled blank that is similar to the containers shown in FIG. 11.

Referring to FIG. 12 there is shown a label area on a pre-assembled blank 1290. The information on label 1292 is located on the front face of the blank 190 and includes information that is associated with a particular patient. The label 1292 may be affixed separately as a separate label, printed on the blank 1210 in the label area, or any combination thereof. The label area includes the top wall 1212, and top side flaps 1216a and 1216b.

Figure 13A:
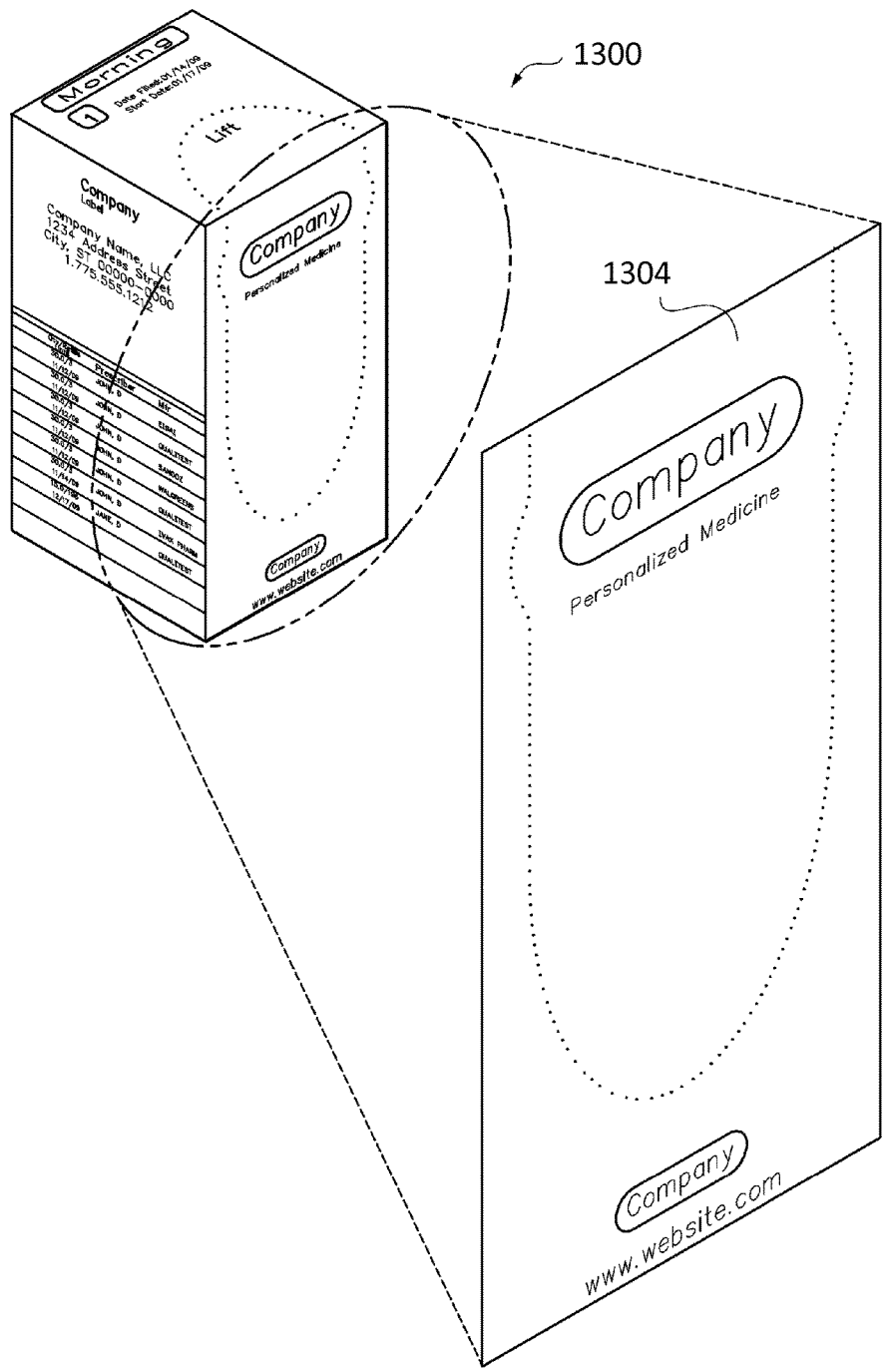
FIGS. 13A-13B show an isometric view of the 30-day tablet dispensing container, with the top and front expanded, respectively.
Figure 13B:
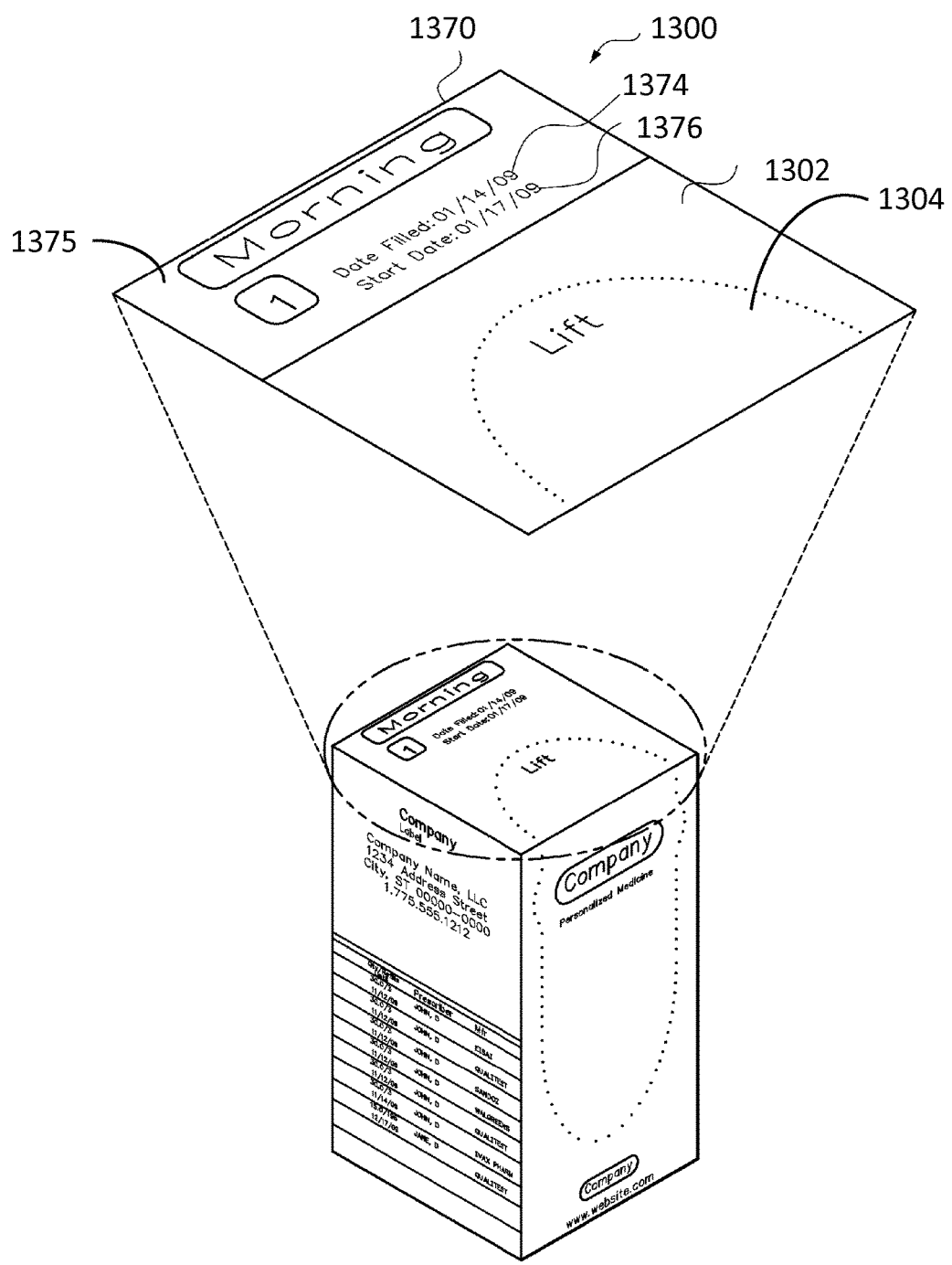

Referring to FIGS. 13A-13B, there is shown an isometric view of the 30-day tablet dispensing container 1300. In general, the illustrative 30-day tablet dispensing container is a foldable box that includes a top wall, a front side wall, a right-side wall, a back side wall, a left-side wall and a bottom wall. The top wall has one end fixedly couple to the foldable box and an opposite end that provides a foldable lid. The front side wall has a removable lid that is bordered by a plurality of perforations. The right-side wall abuts the front side wall and the top wall. The back side wall abuts the right-side wall and the top wall. The left-side wall abuts the top wall and is between the back side wall and the front side wall. The bottom wall abuts the front side-wall, the right-side wall, the back side, and the left-side wall. The container is formed to receive a plurality of pouches as described herein.

By way of example and not of limitation, the illustrative cardboard used to construct container 1300 includes an outer smooth layer of paper and a thick interior layer. The outer smooth layer may receive printed text or images using an illustrative laser printer, ink jet printer, or other such printing means. Additionally, the outer layer may also be configured to receive a label that is affixed thereto.

In the illustrative embodiment, a perforated, removable lid 1304 makes up a large portion of the front side wall 1306 and top wall 1302 of the illustrative container 1300. The lid can be partially or completely removed in order to access the medicament pouches within the container 1300. In one embodiment the lid 1304 may only occupy one wall such as the front side wall. In the illustrative embodiment, the lid occupies the front side wall 1306 and extends to the top wall 1302.

The illustrative top wall 1302 has one end fixedly coupled to the foldable box and an opposite end that provides a foldable lid. A secondary label (not shown in exploded view) is configured to seal the foldable lid on the top wall. In the illustrative embodiment, the secondary label has a bar code and includes the time interval when the tablets should be administered or taken. In the illustrative embodiment, the secondary label 1375 visible on top wall 1302 of the container 1300 indicates the time period 1370, the filling date 1374, and the prescription start date 1376 listed above the perforations of lid 1304.

Figure 14A:
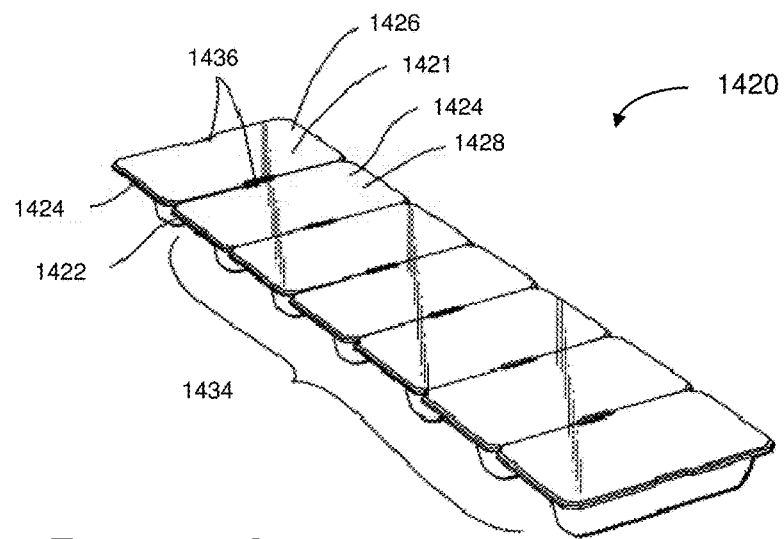
FIGS. 14A-14B show a top view and a bottom view of a plurality of illustrative sealed multiple prescription containers.
Figure 14B:
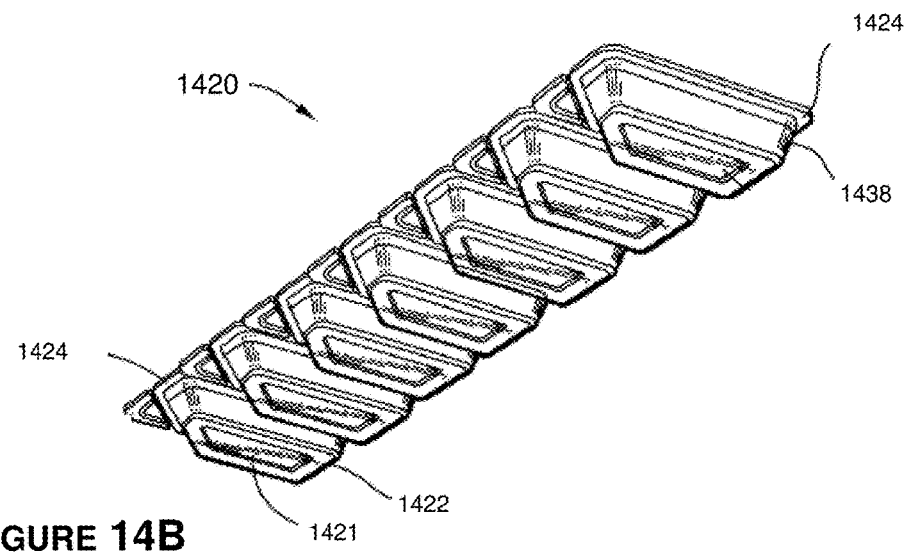

Referring now to FIGS. 14A-14B, a top view and a bottom view of a plurality of illustrative sealed multiple prescription containers 1420 is shown. Both views reflect that one of the containers 1421 comprises a tapered body container 1422 with a cavity for holding a plurality of tablets. The tapered body container 1422 allows a plurality of individual containers to be stacked for storage. Each container 1420 has a flanged top surface 1424 configured to be sealed with a lid 1426. In certain embodiments, the tablet assembly may require individual containers that vary in depth depending on the amount of tablets needed to be dispensed at a specific time. While the depth of the individual containers may vary, the flanged top surface and collar remain constant for processing of different sized individual containers and for commonality with the assembly sleeve.

In one embodiment, the multiple prescription container assembly comprises a plurality of individual containers. In one illustrative embodiment, container 1421 is coupled to container 1428 with lid 1426. The lid 1426 seals one or more containers. The sequential connection enables a linear configuration for the individual containers.

However, it should be noted that the quantity of containers in a multiple prescription assembly may vary as well as the interconnection configuration of the containers, e.g. a circular, an elliptical, polyhedral, etc.

In another embodiment, the plurality of multiple prescription containers are made from a single piece of moldable material having a plurality of indentations wherein each indentation is configured to form one container 1421 in the set of containers 1434. At least one of the containers is configured to receive a first tablet associated with a first medication, and a second tablet associated with a second medication that is different from the first medication. The set of containers 1434 are connected to one another by frangible connections 1436 or perforations positioned within the flanged edge 1424 that are proximate to the adjacent container. The frangible connection 1436, which is between containers, allows the containers to "break-away" from the set of containers 1434 in a sequential manner. Once the lids are attached and/or sealed to the top flanged surface 1424, this sequential connection enables a linear configuration as described above.

Each container may also comprise a collar 1438 below the flanged edge 1424 that allows the containers to be stored in a stackable configuration. Stacking of the containers can also be performed with the collar 1438. Each container may also comprise a bottom surface 1440 with at least one ridge 1442. The ridge is useful in minimizing tablet-to-tablet collisions and avoiding medication sloughing off of a tablet due to collisions with other tablets. By limiting excessive movement of the tablets in each of the containers, the ridge or ridges on the bottom of the container(s) help preserve the integrity of the tablets within. The ridge may protrude outward from the bottom surface of the containers, or in other embodiments, may be formed by an indentation of the bottom surface. The ridge(s) may be configured as a square, rectangle, circle, and a plurality of parallel lines as well as other geometric shapes.

The illustrative set of containers 1434 comprises seven adjacent containers configured for sequential dispensing of the contents of each container. Sequential dispensing refers to individual containers being "dispensed one at a time," which is different from being "cherry picked" from a grid of individual containers. The number of containers in a set of integrated containers may vary due to the prescription prescribed for the user. While the illustrative embodiment describes seven containers, a set of containers may comprise at least two containers to about 20 containers, and more preferably about 10 to about 14 containers. It is expected that most of the containers will be of similar size for ease of filling the containers, but in certain embodiments varying container sizes may be needed. The set of containers 1434 may be opaque but in preferred embodiments, the moldable material is sufficiently transparent for the user to see the contents of the containers.

The illustrative lid 1426 of container 1421 comprises a printing surface where unique prescription-specific information is displayed for each container. The information displayed on the printing surface may include, but is not limited to, the patient's name, the date and the day of the week the contained mixed dosage medications (tablets) are to be taken, as well as the time of day that the tablets are to be taken. The markings on the containers inform the patient and/or caregiver the time in which the contents of the container are to be taken in the proper sequence. In general, the lid stock comes from a roll and the appropriate amount of lidstock is released from the roll to accommodate the designated number of containers to be sealed. For a thermoformed container, using polypropylene for the material for the lid stock, an unsealed area of lid film is generally used to help in the peeling of the lid. The breakaway tab 1432 on the illustrative container 1421 gives the user something to hold onto and is a useful feature to a container that is manufactured by injection molding with plastics like polyethylene or styrene.

Figure 15:
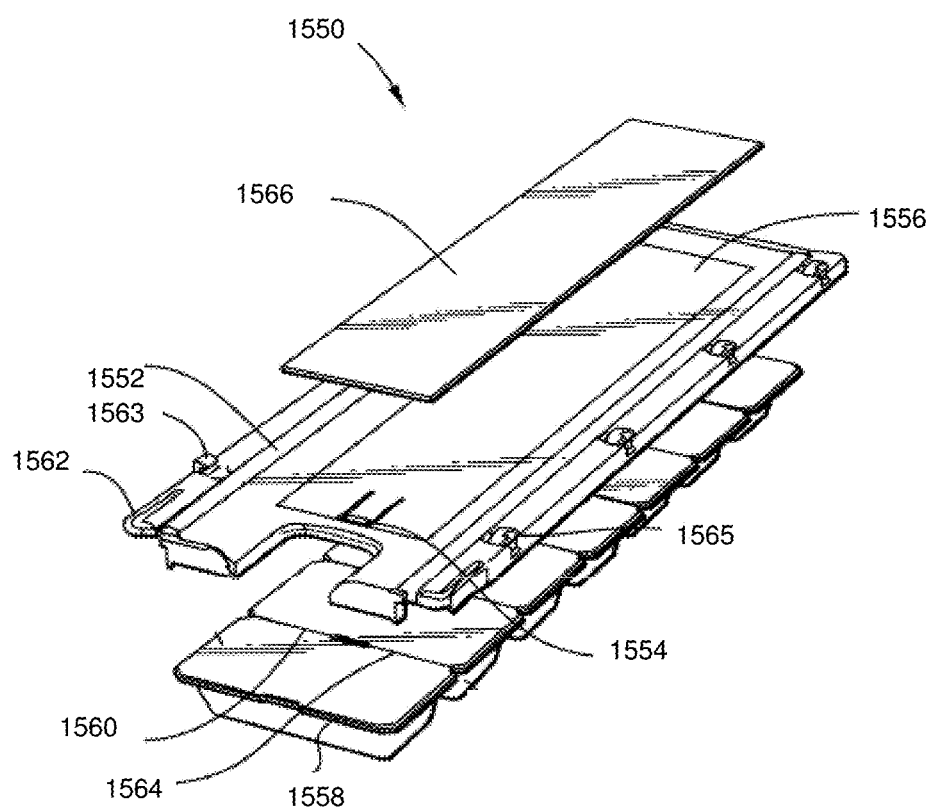
FIG. 15 shows an exploded isometric view of an illustrative multiple prescription container assembly.

Referring to FIG. 15 there is shown an exploded isometric view of the multiple prescription container assembly 1550 prior to being assembled. The exploded view also shows a top tab 1554 on the top surface 1556 of the sleeve which holds the end container 1558 by catching the rectangular void made by one of the indentations 1560. When the user pushes down the sleeve tabs 1562, the set of sealed containers are released and the top tab 1554 is disengaged from the containers. The end container 1558 can be slid out of the dispensing sleeve 1552 if there are no other child protective features, and the top tab latches on to the next indentation (not shown). The user then can break the frangible connection 1564 and remove the container. This two-step process of holding tabs 1562 and pulling on the end of the sealed containers is a "child safety" feature. It shall be appreciated by those skilled in the art that certain embodiments can be made to conform to a more senior-friendly solution that is described in further detail below.

Additionally, there is shown a notch 1563 that is configured to be fit into an illustrative cavity that is a square-shaped perimeter 1565 and receives a notch similar to notch 1563. The notch 1563 permits two dispensing sleeves to "snap" together. The square shaped perimeter 1565 is located on the edge of the dispensing sleeve 1552 and has a square cut and a lip. Printed material 366 may be attached to the top surface 1556 of the dispensing sleeve 1552. Additional information about the prescription or other patient data can also be placed on the dispensing sleeve 1552. The dispensing sleeve 1552 may also comprise a surface for printable indicia, and the printable indicia may include patient data as well as prescription information.

Figure 16:
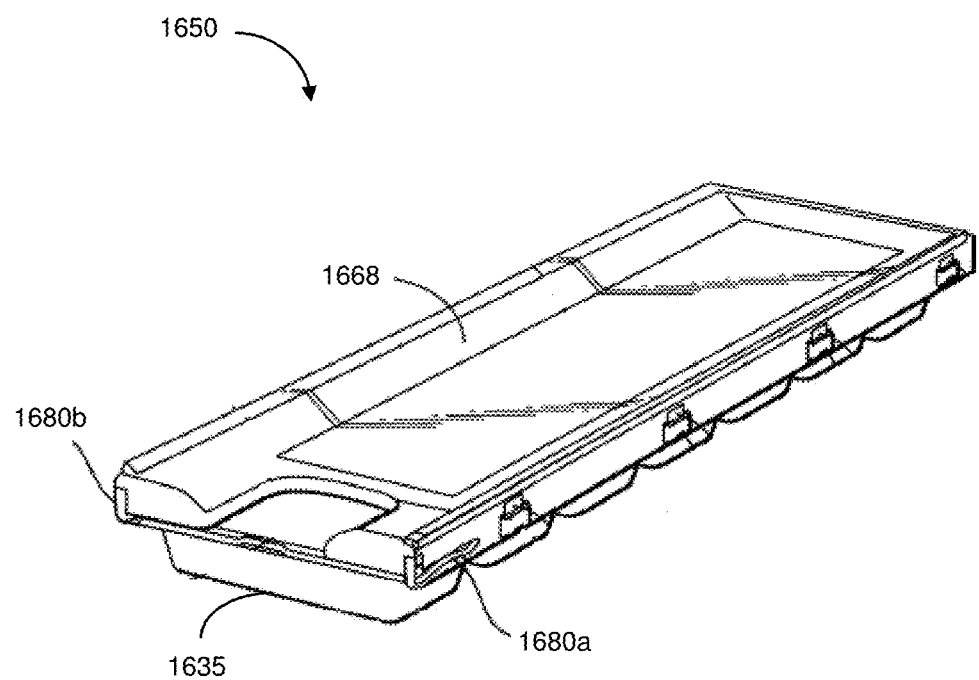
FIG. 16 shows an isometric view of an illustrative multiple prescription container assembly.

Referring to FIG. 16 there is shown an isometric view of the multiple prescription container assembly 1650. The end container 1635 can be slid out of the dispensing sleeve 1668 if there are no other child protective features, and the top tab latches on to the next indentation (not shown). The user then can break the frangible connection and remove the container. This two-step process of holding tabs 1680*a* and 1680*b* and pulling on the end of the sealed containers is a "child safety" feature. It shall be appreciated by those skilled in the art that certain embodiments can be made to conform to a more senior-friendly solution that is described in further detail below.

Figure 17:
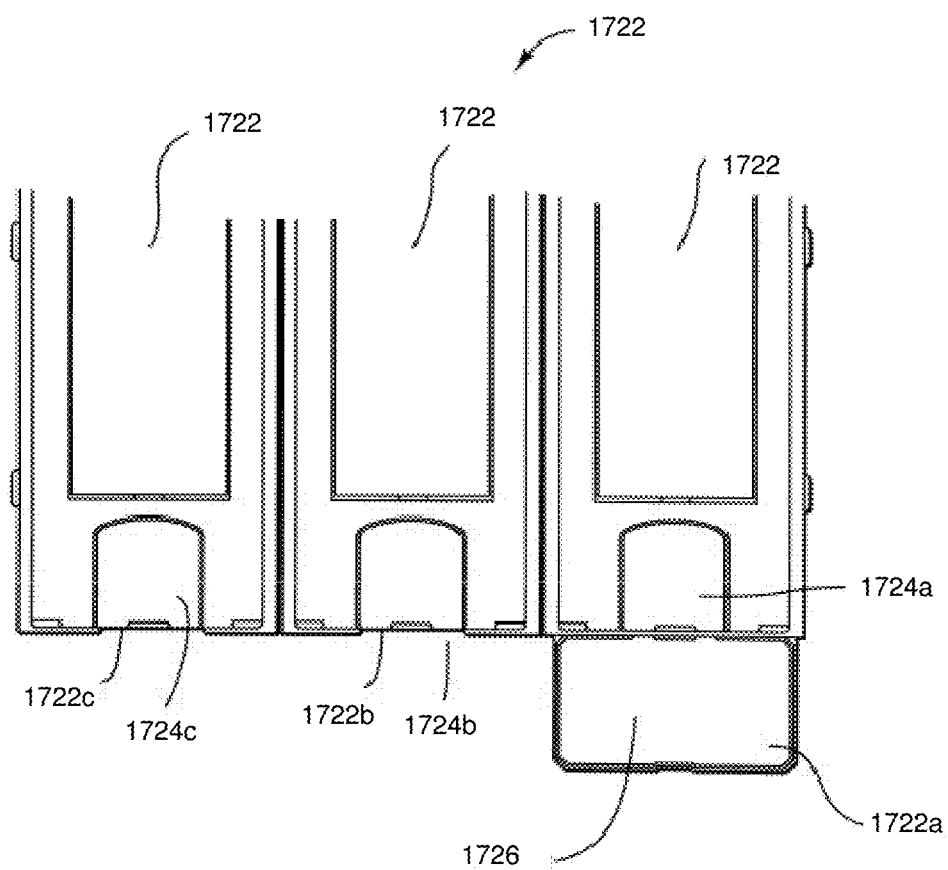
FIG. 17 shows a top plan view of a plurality of illustrative multiple prescription container assemblies, coupled to one another.

FIG. 17 is an illustrative top view of multiple sleeves coupled to one another and depicting the sequential dispensing of a container. In this illustrative example, the multiple prescription container assembly is for patients that must take multiple medications more than once a day. The multiple prescription container assembly 1720 comprises a plurality of thermoformed (or molded) sets of sealed container 1722*a*, 1722*b*, and 1722*c* that are heat sealed with a laminated lid 1724*a*, 1724*b*, and 1724*c*, respectively. Each container within the set of containers 1722*a*, 1722*b*, and 1722*c* contains the required medications that have been prescribed for a particular time. The containers are separated by perforations as described above. In the illustrative embodiment, each container contains printed markings 1726 that identify the medications contained therein, and may also indicate the patient's name, and, most importantly for the purposes of this embodiment, the day and the time of day that the medications are to be taken.

In the illustrative embodiment of FIG. 17, each container is dedicated solely to a particular time of day. In the illustrative example, the set of containers 1722*a* are taken in the morning, the set of containers 1722*b* are taken at approximately noon, and the set of containers 1722*c* are taken in the evening. Thus, it is possible to have a plurality of containers for each day of the week so that each container has the proper dosage that is to be taken at a particular time of day. In this illustrative embodiment, the patient is supplied with a complete set of containers for a particular week for a specific time of day.

Each individual container within each set of containers is to be taken at the correct, prescheduled time each day as marked on each container. The multiple prescription container assembly 1720 may be provided to the patient or caregiver as three separate sets of containers enclosed in three separate dispensing sleeves. The patient or caregiver can interlock the three separate dispensing sleeves 1728*a*, 1728*b*, and 1728*c*.

Figure 18A:
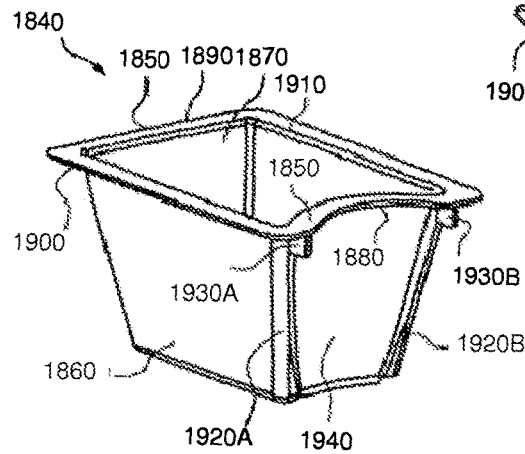
FIGS. 18A and 18B are perspective views of another embodiment of a medicament container.
Figure 18B:
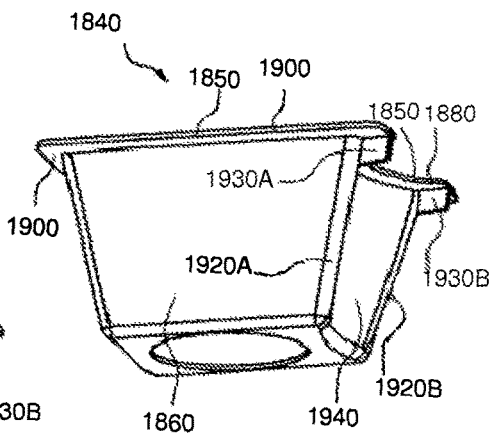
Figure 19:
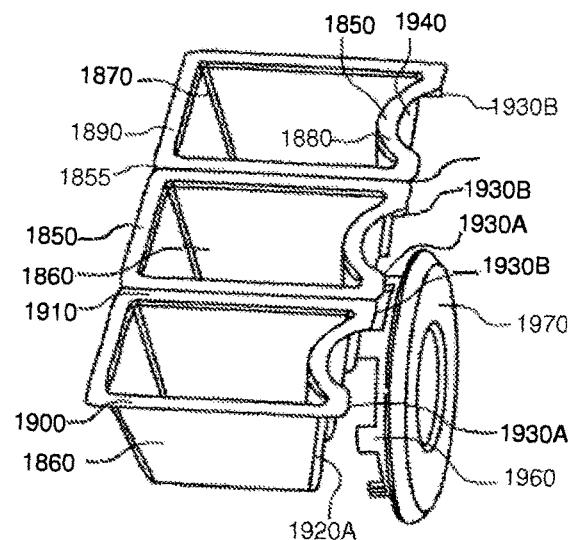
FIG. 19 is a perspective view of a compliance wheel interacting with one of a plurality of medicament containers.

FIG. 18A, FIG. 18B and FIG. 19 show one embodiment of a medicament container or cup 1840 for holding medication in the form of tablets, caplets, pills, capsules, powders, liquids, gels, suppositories or other form of medication. The medication within containers 1840 may be prescription medication, vitamins, supplements, herbal formulations, or combinations thereof, intended to be ingested by or administered to a patient to improve the patient's health or well being. The medicament container 1840 comprises a tapered body 1860 with a cavity 1870 for holding a plurality of pills or other medication. The container 1840 includes a flanged top surface or edge 1850 configured to be sealed with a lid (not shown). Container 1840 may also include a frangible or removable top or lid (not shown) adjacent to flange 1850. Breaking or removing the top allows a user to access the medication therein. The top may be transparent to allow a user to see the contents of container 1840.

Generally, the flanged top edge 1850 of container 1840 comprises a first side 1880 and second 1890 side which are configured such that flange 1850 interacts with the spiral grooves or tracks of a packaging system such that container 1840 can slide or otherwise move along the tracks. The flange top edge 1850 further comprises a third side 1900 and fourth side 1910. When containers 1840 are arranged in a chain, side 1900 of one container 1840 is positioned adjacent side 1910 of an adjacent container (except for the first container 1840 in the chain). Top edge sides 1900 and 1910 of adjacent containers 1840 can be connected to one another by a frangible interface 1855. The containers 1840 can then be detached from one another by breaking the connector 1855.

Each container 1840 includes protrusions or ribs 1920A, 1920B on the exterior of tapered body 1860 of the container 1840. Ribs 1920A and 1920B each support a tab section 1930A and 1930B respectively, with tabs 1930A, 1930B located adjacent top flange 1850. The tabs 1930A and 1930B are configured to interact with sprocket teeth on compliance wheel 1960 to allow the container 1840 to be moved as teeth 1960 apply force to tabs 1930A, 1930B when wheel 1970 is rotated. The ribs 1920A and 1920B and tabs 1930A and 1930B may in many embodiments be configured to aid in childproofing the packaging system, as described further below. Counter-clockwise rotation of wheel 1960 results in teeth 1970 applying force to tab 1920A to move container 1840 in one direction, while clockwise rotation of wheel 1950 results in teeth 1970 applying force to tab 1920AB to move container 1840 in the opposite direction.

The tapered body 1860 of each container 1840 further comprises an arcuate or concave portion 1940 positioned between the ribs 1920A and 1920B. Top flange 1850 includes an arcuate or concave portion adjacent to the concave portion 1940 of container body 1860. The configuration of the concave portions 1940 and 1950 of the container 1840 allows the teeth 1970 of compliance wheel 1960 to engage the tab portions 1930A, 1930B of the container 1840 without interference from the tapered body 1860 of the container 1840.

Figure 20:
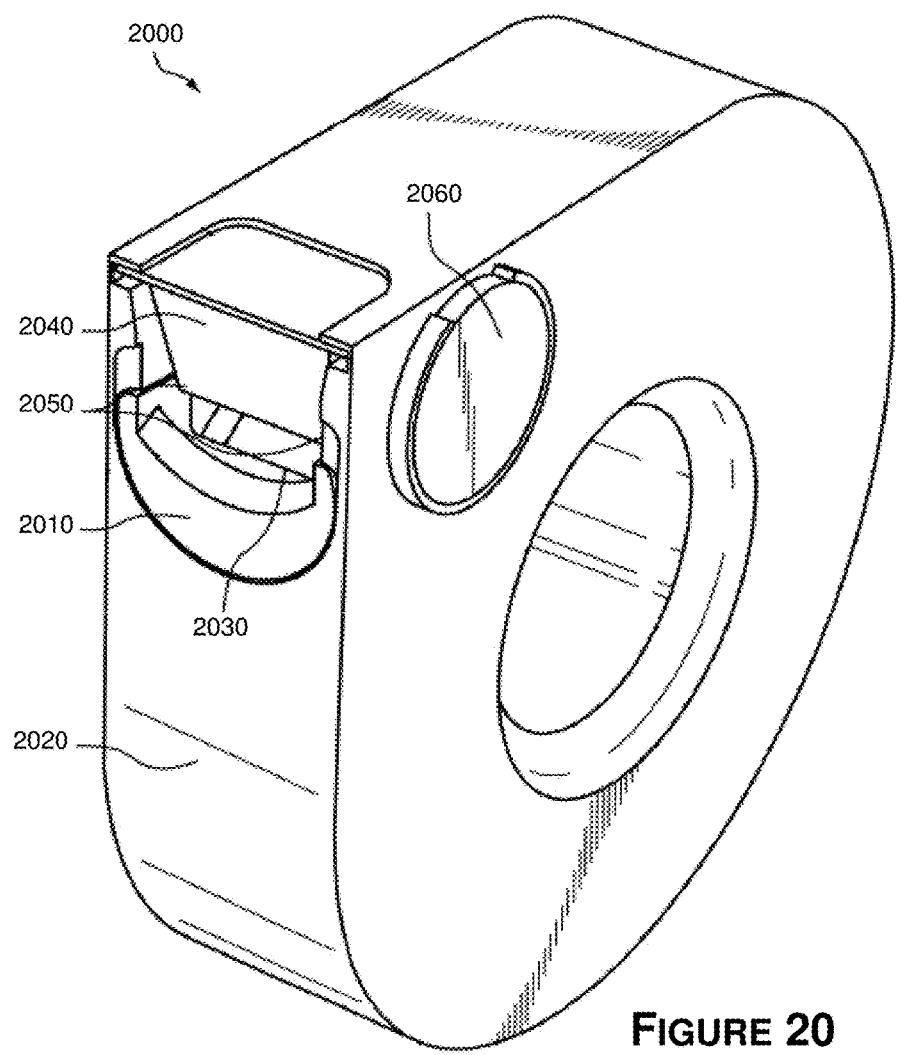
FIG. 20 is a perspective view of an embodiment of an illustrative spiral packaging system with a transparent exterior, shown with a compliance wheel and a plurality of medicament containers.

Referring now to FIG. 20, there is shown still another embodiment of a medication packaging system 2000, wherein like reference numbers are used to denote like parts. The spiral medication packaging systems may be modular and attachable to each other to form extensible or scalable medication packaging systems in a similar manner as described above. The apparatus 2000 includes a child proofing barrier element 2010 movably mounted in wall 2020 adjacent to opening 2030. Barrier 2010 is movable between an open position (as shown in FIG. 20) that allows container 1840 to pass through opening 2030, and a closed position (not shown) wherein container 1840 is blocked by barrier 2010 such that container 1840 cannot exit or be removed through opening 2030. A spring or bias element (not shown) may be operatively coupled to barrier 2010 such that barrier 2010 remains in the closed position unless a user applies sufficient force to barrier 2010 to overcome the bias and move barrier 2010 to the open position.

In the embodiment of FIG. 20, barrier 2010 includes an arcuate or curved lip 2040 that is configured to cover and block corners 2050 of container 1840 when barrier 2010 is in the closed position, and which allows corners to pass over or clear lip 2040 when barrier is in the open position as shown in FIG. 20.

To operate the apparatus 2000, a user simultaneously pushes on or depresses barrier 2010 to the open position while advancing compliance wheel 2060 to move container 1840 through opening 2030. When the container 1840 has passed through opening 2030, the container 1840 is detached and removed from the apparatus 2000, and the barrier 2010 is released to return to the closed position. The next container 1840 is then blocked by barrier 2010 from exiting the apparatus 2000 until the child proofing barrier 2010 is again depressed or moved to the open position. Simultaneous manipulation of the compliance wheel 2060 and barrier 2010 are sufficiently difficult that small children are unable to access the medication within apparatus 2000.

Figure 21:
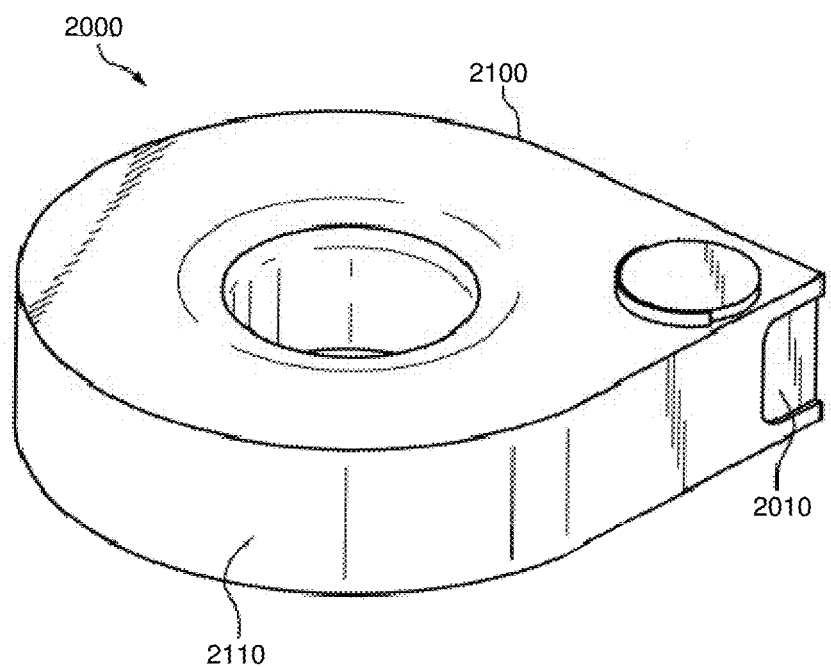
FIG. 21 is a perspective view of an illustrative spiral packaging system.

Referring now to FIG. 21 there is shown an isometric view of the spiral medication packaging system 2000 in accordance with the invention, wherein like reference numbers denote like parts. The apparatus 2100 includes transparent outer facings or housing elements. Housing element 2110 is visible on the apparatus 2100 in FIG. 21.

Figure 22:
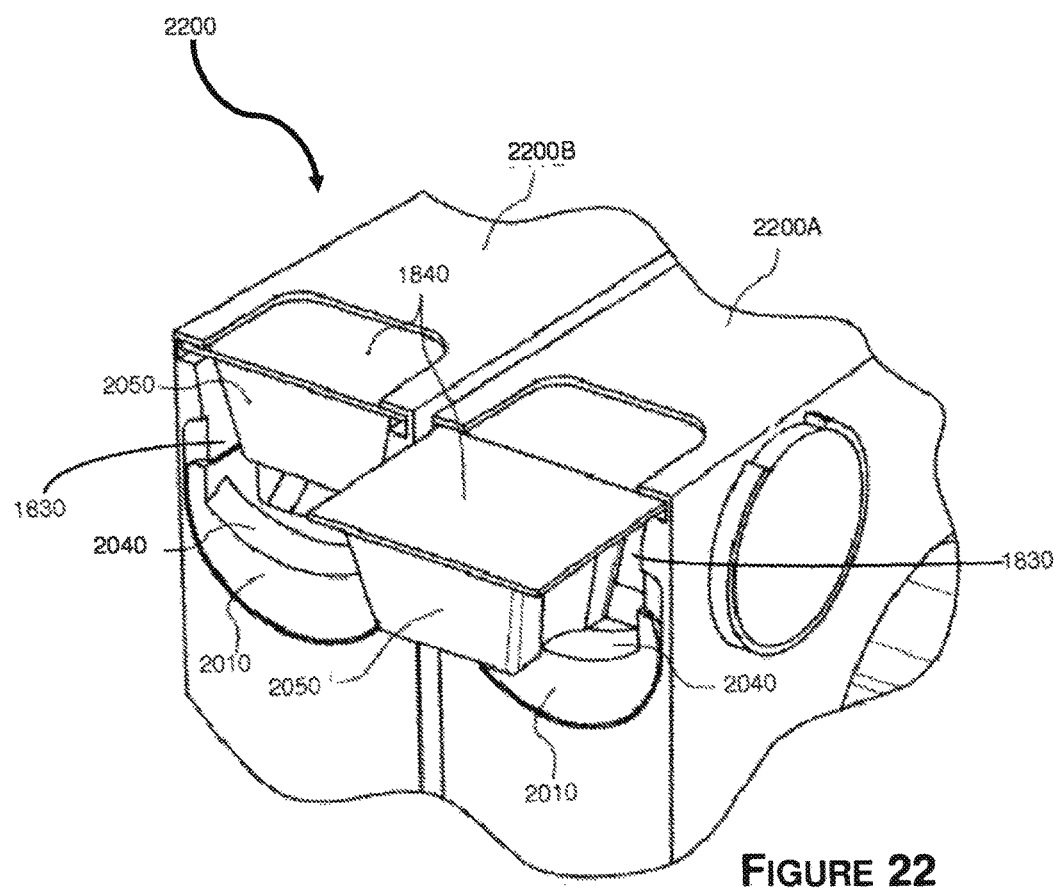
FIG. 22 is a perspective view of a portion of the child proof mechanism of the illustrative spiral packaging system of FIG. 21.
Figure 23:
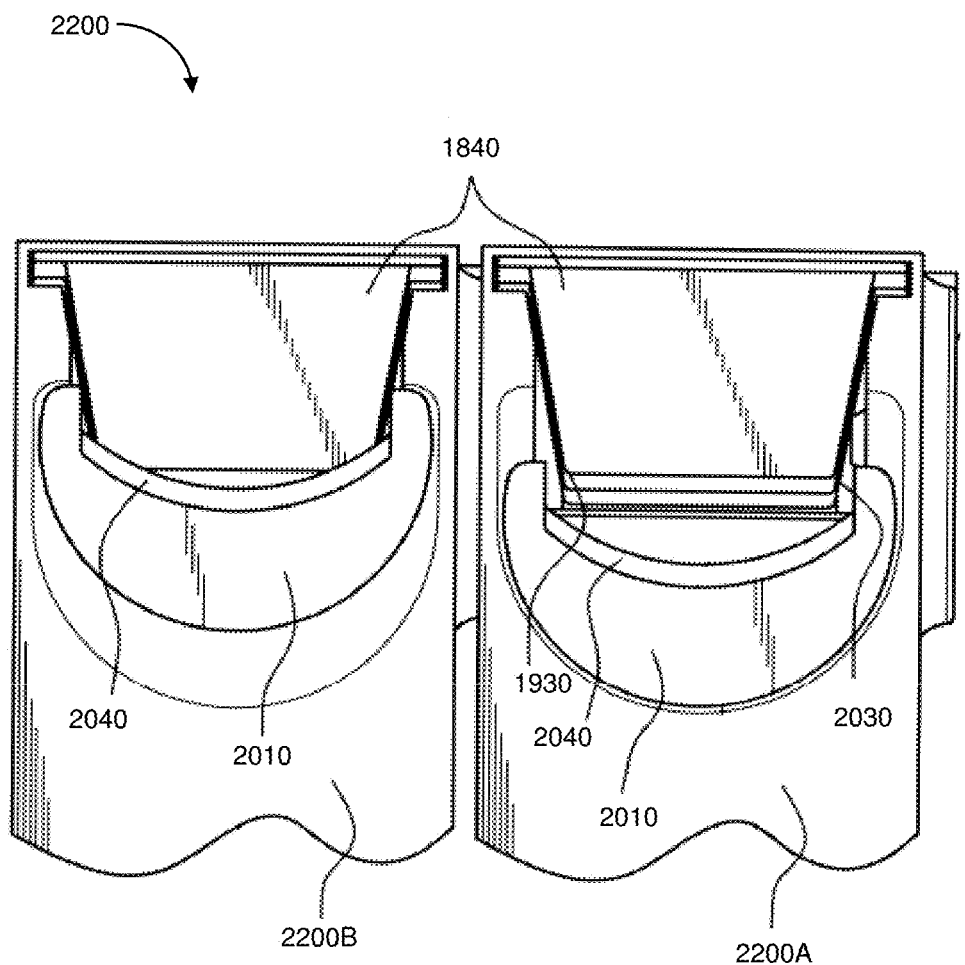
FIG. 23 is a front elevation view of the portion of the child proof mechanism of the illustrative spiral packaging system of FIG. 21 showing operation of the child safety component.

Operation of the child proof barrier 2010 will be more fully understood by making reference to FIGS. 22 and 23, wherein like reference numbers denote like parts. FIGS. 22 and 23 show a portion of a modular system 2200 wherein the child proof barrier 2010 in packaging system 2200B is shown in the closed position, and wherein the barrier 2010 is shown in the open position in adjacent packaging system 2200A. In the closed position as shown in system 2200B, arcuate lip 2040 of barrier 2010 blocks the lower corners of container 1840 to prevent container 1840 from being removed through opening 1830. In the open position shown in system 2200A, the lower corners 2050 of container 1840 are clear of lip 2040 and container 1840 may be advanced through opening 2030 by operation of compliance wheel 2110. The arcuate shape of lip 2040 accommodates a user's finger and facilitates manipulation of barrier 2010 and container 1840.

Figures 24A, 24B, 24C:
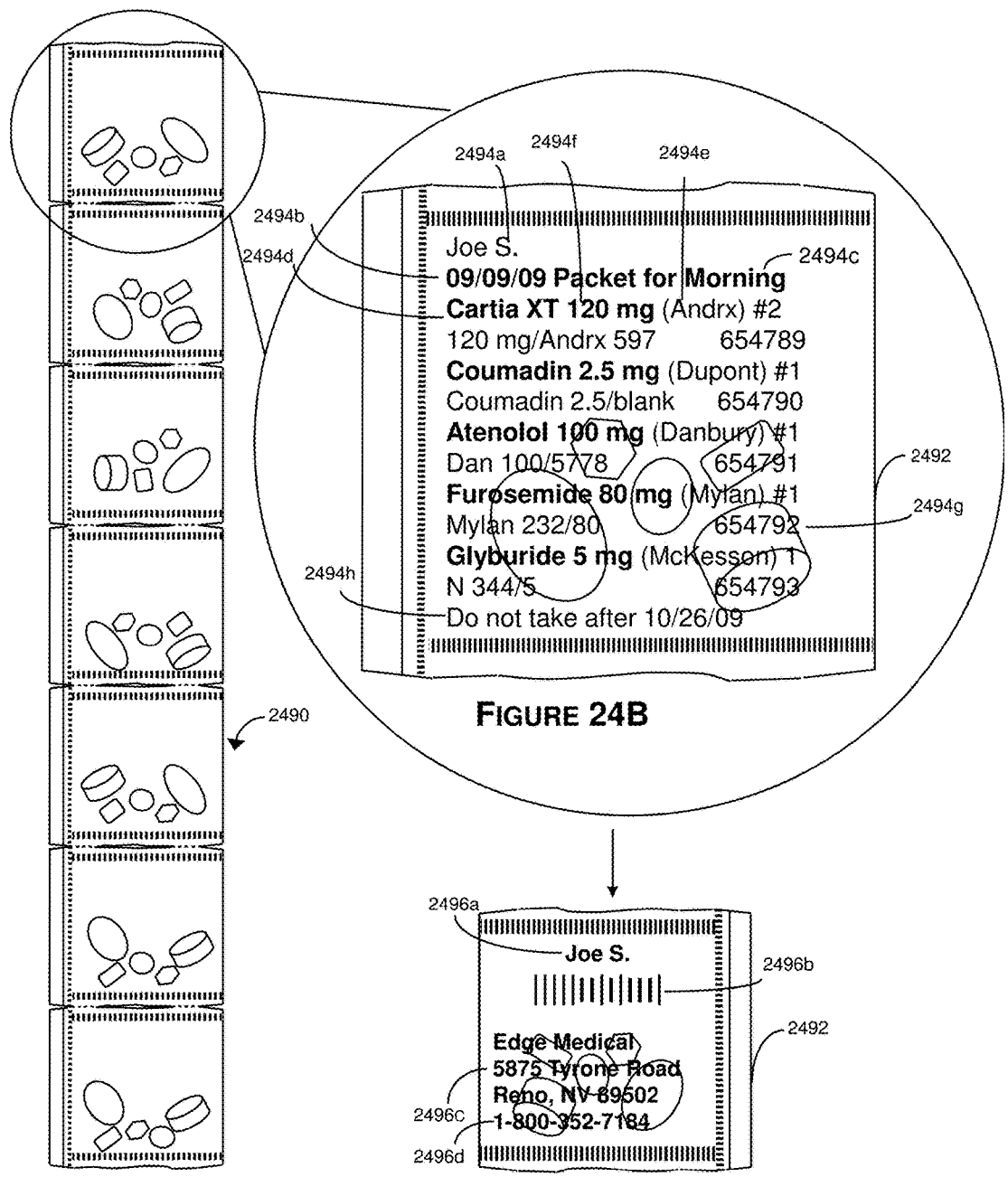
FIG. 24A shows a group of seven separable pouches, wherein each pouch comprises a plurality of different tablets.
FIG. 24B shows an exploded view of the illustrative front side of one of the sealed center cut pouches that is included in the strip of pouches.
FIG. 24C shows an exploded view of the illustrative back side of the pouch in FIG. 24B.
Figure 25A:
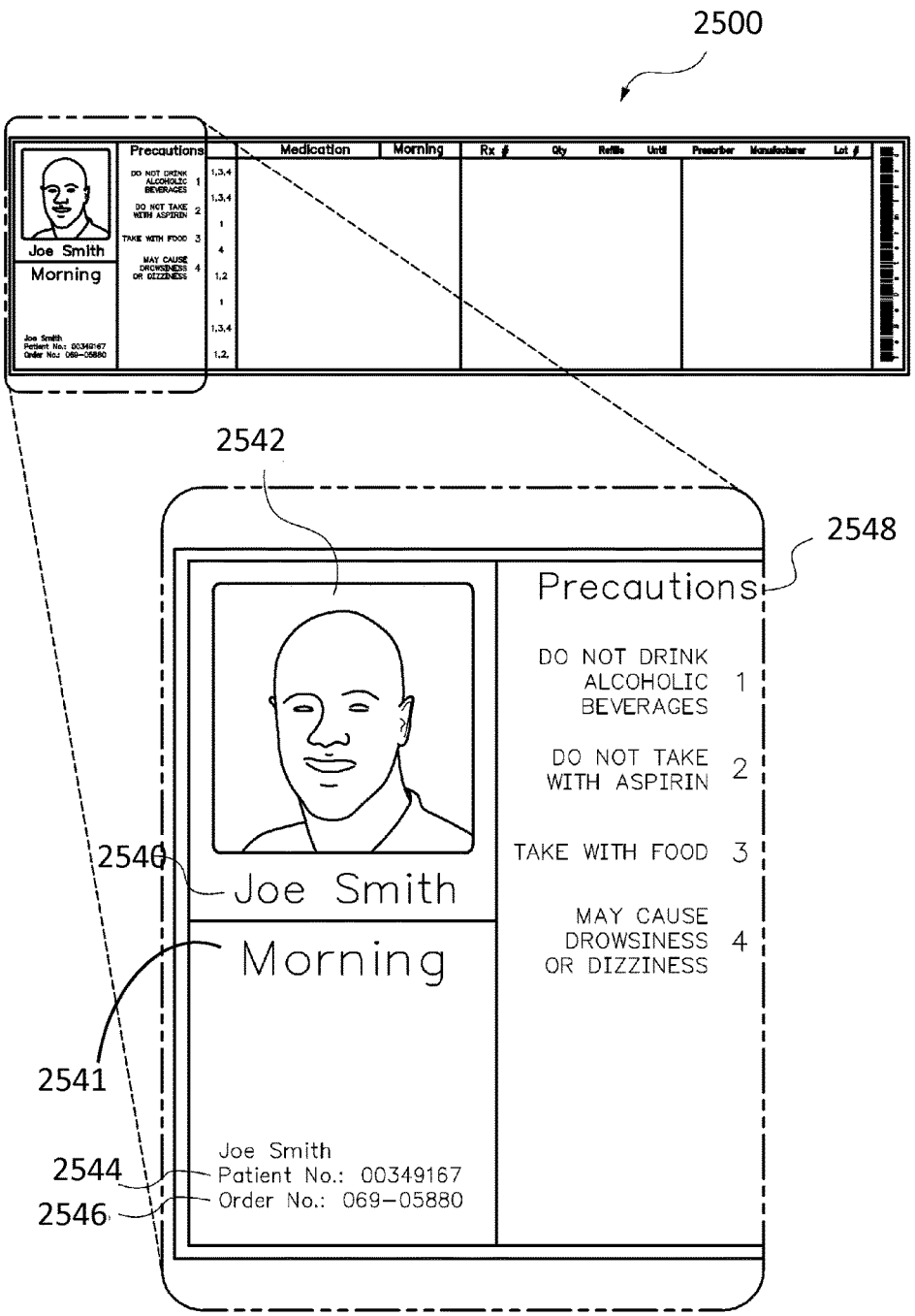
FIGS. 25A-25G show an illustrative label on the folded box.
Figure 25B:
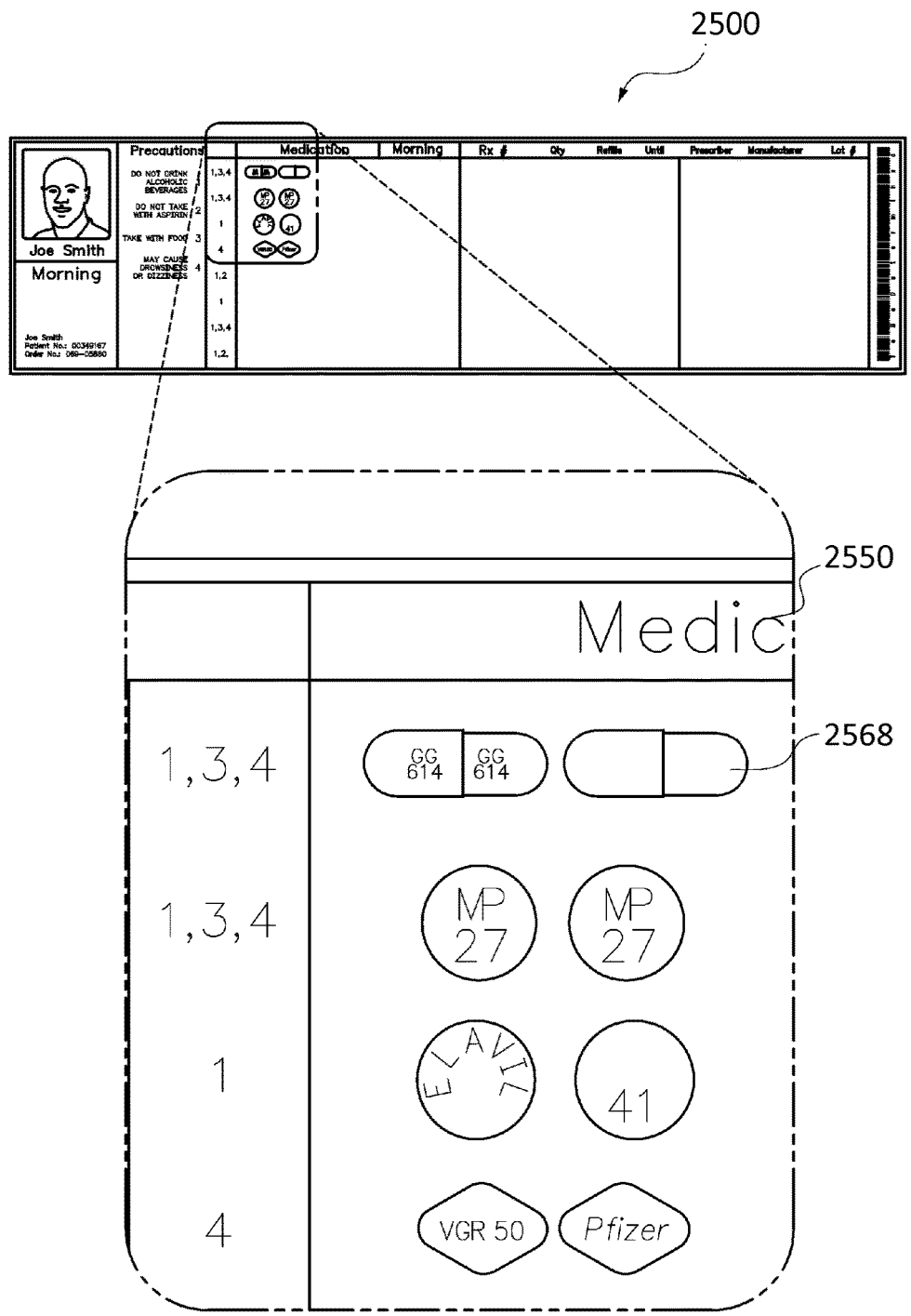
Figure 25C:
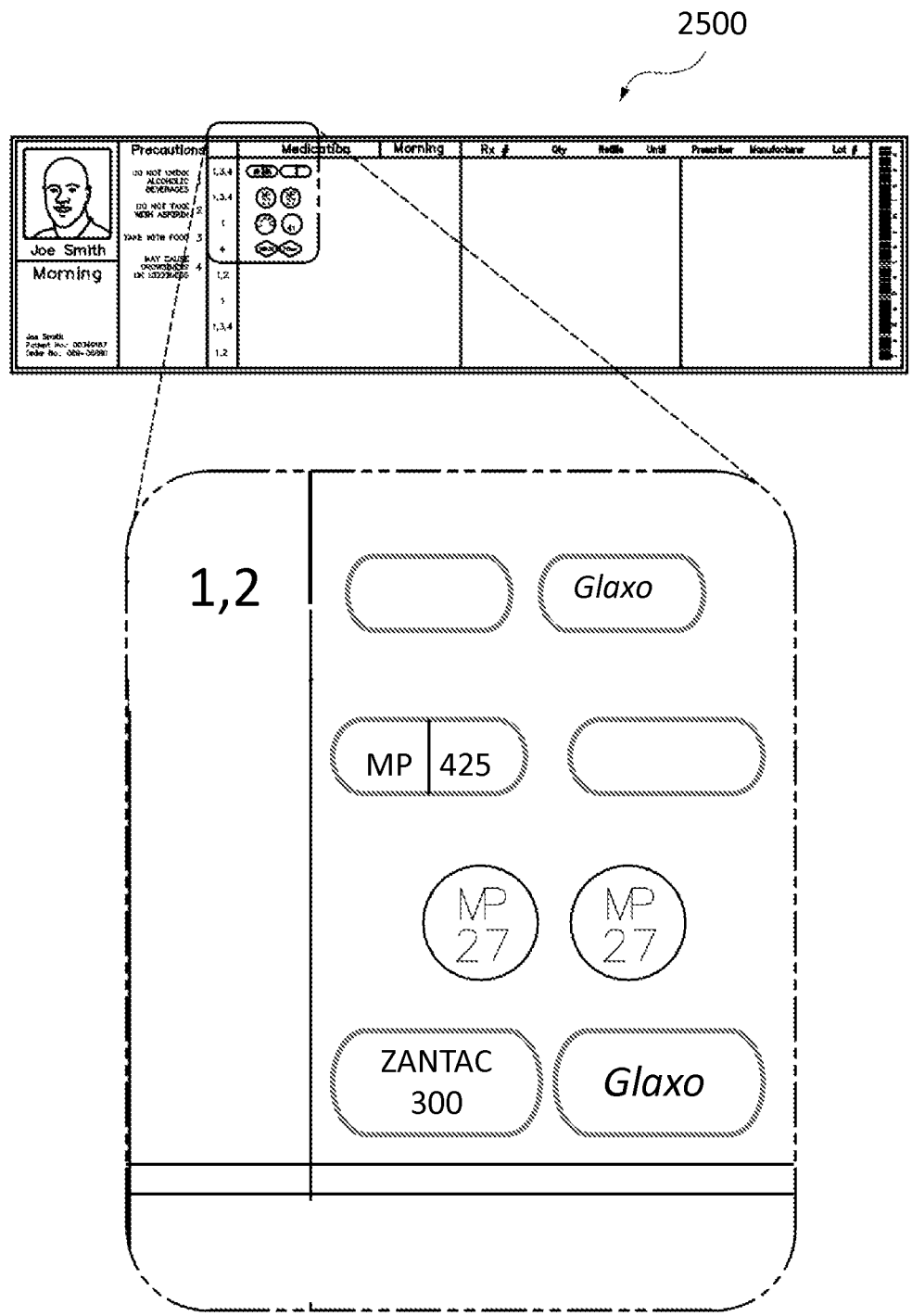
Figure 25D:
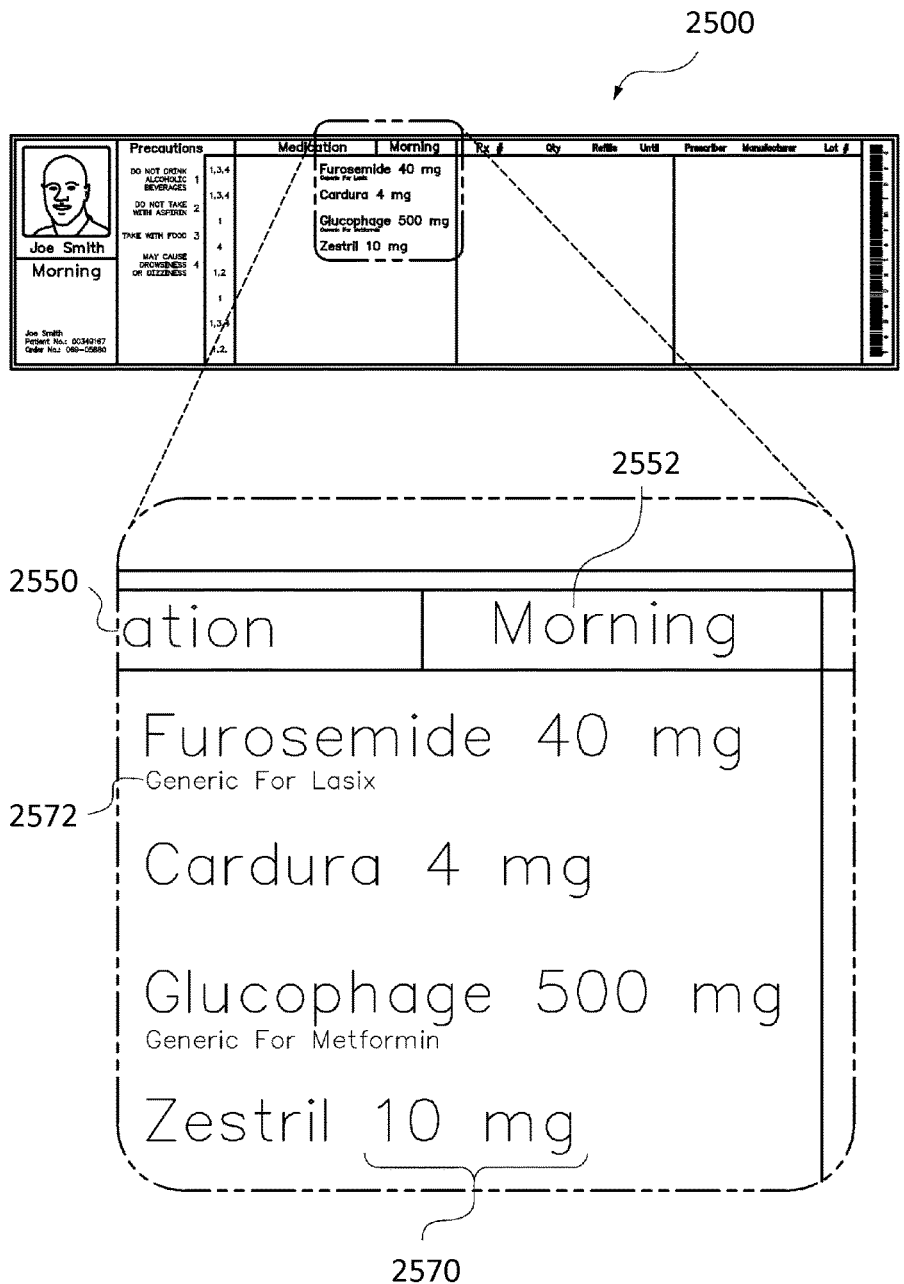
Figure 25E:
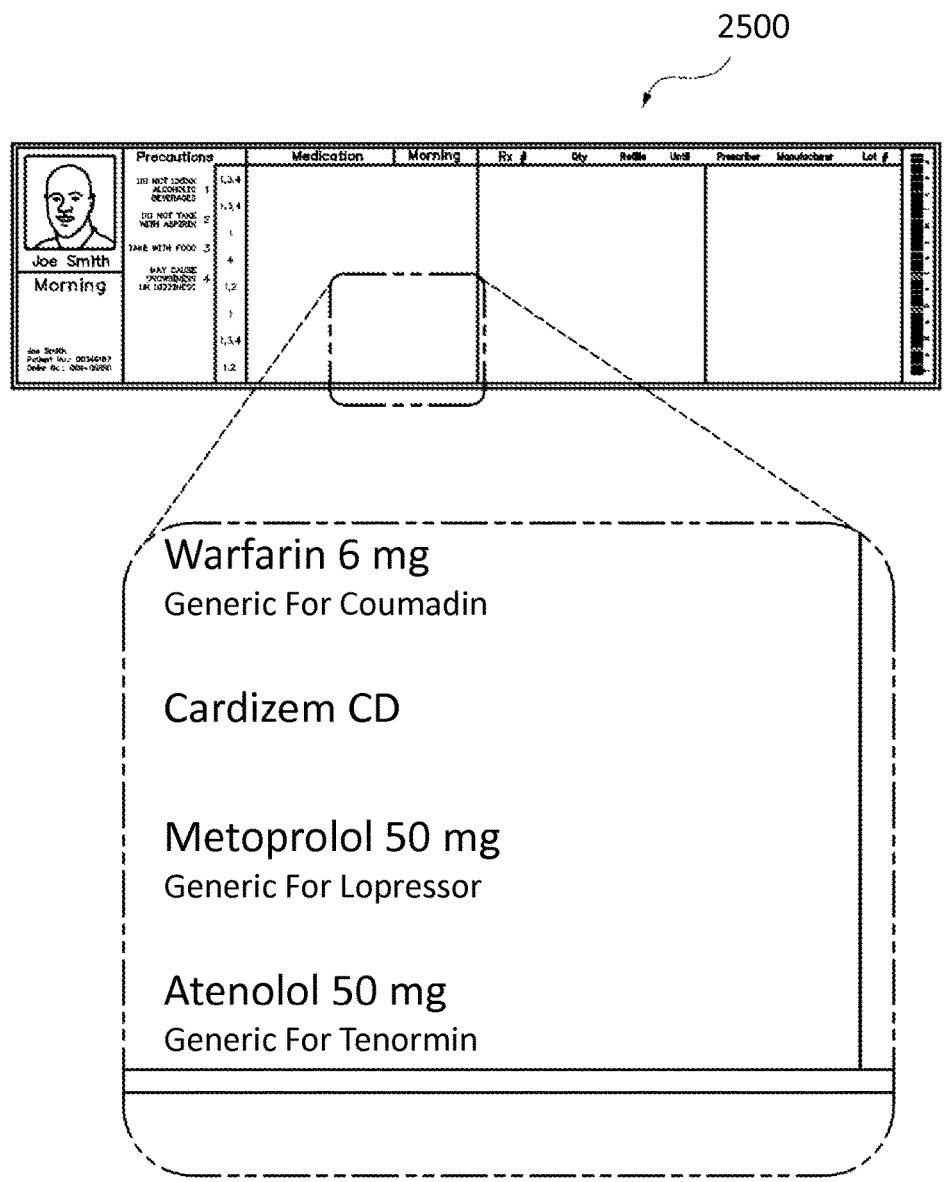
Figure 25F:
Figure 25G:
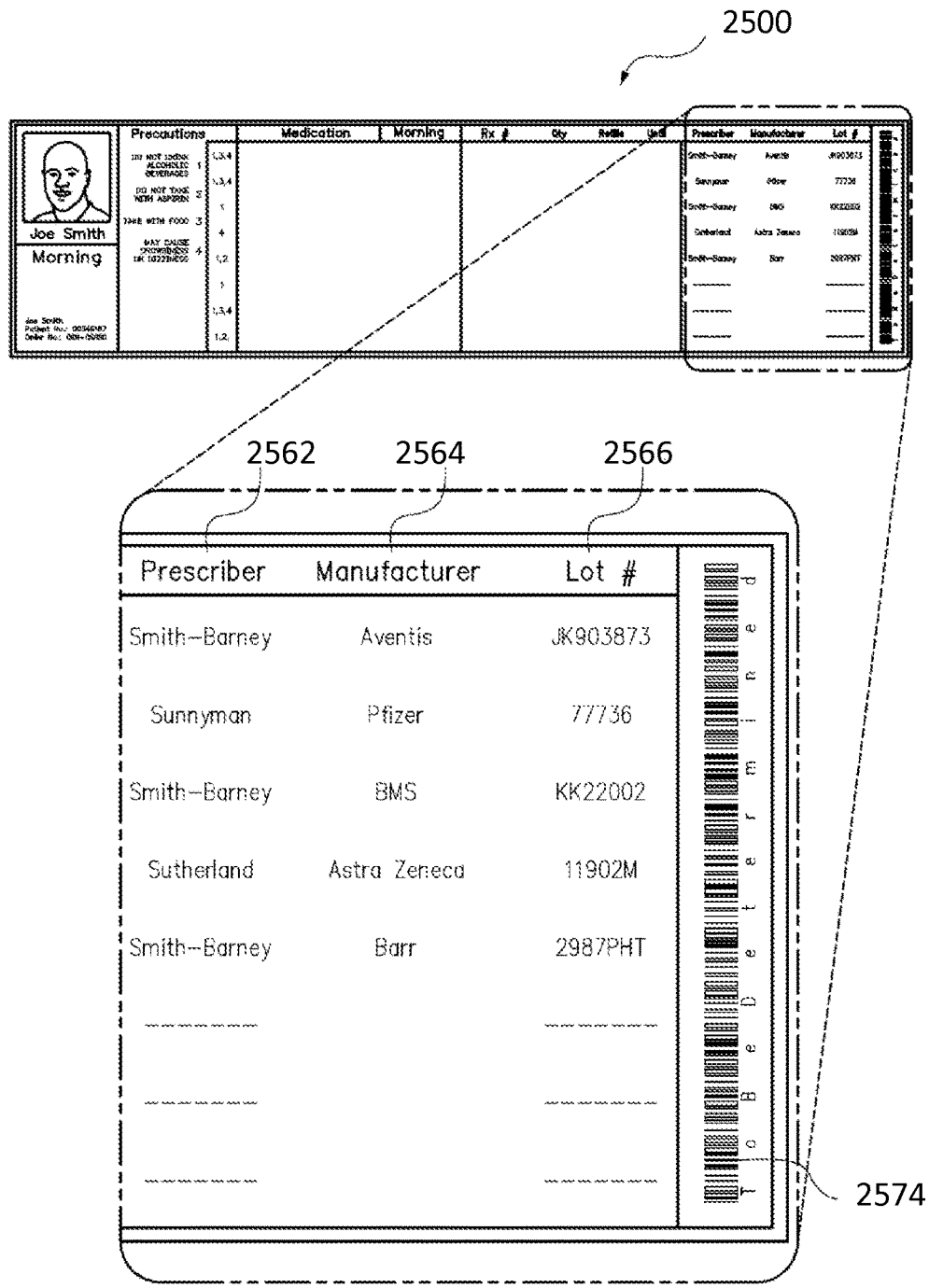

During the filling process, integrated labeling is produced and affixed to the medicament containers. Integrated labeling is a unique feature of the system and methods described herein. Integrated labeling includes information about the patient, the medications the patient is taking, and other illustrative information. Integrated labeling may include extensive labeling on the primary medicament containers (such as the pouches or medicament cups that directly hold the medication. One illustrative example of this labeling is shown in FIGS. 24A-24C. Integrated labeling may also include extensive labeling on the secondary container that may hold a plurality of primary containers, as shown in FIGS. 25A-25G. Integrated labeling may also include a Patient Information booklet. Illustrative integrated labeling is described in more detail below.

Referring to FIG. 24A there is shown a group of seven separable pouches, wherein each pouch comprises a plurality of different tablets. The separable sealed pouches have been grouped into a collection of seven pouches 2490 that correspond to a seven day supply of medications. A plurality of sealed pouches that is grouped is also referred to as a "strip," and the terms "strip," "group of pouches," and "strip of pouches" is used herein interchangeably.

Referring to FIG. 24B there is shown an exploded view of the illustrative front side of one of the sealed center cut pouches 2492 that is included in the strip of pouches 2490. The exploded view shows that a variety of data fields that are printed on the front of each pouch. In general, the data fields provide information corresponding to each tablet within the pouch. The data fields includes: the name of the patient 2494*a*; the date the tablets should be consumed 2494*b*; the time of day the tablets should be taken 2494*c*; the name of the prescribed medication 2494*d*; the name of the corresponding generic 2494*e*; the dosage 2494*f*; and the prescription number 2494*g*. Additionally, an expiration date 2494*h* is included that identifies the medications should not be taken after the expiration date.

Referring to FIG. 24C there is shown an exploded view of the illustrative back side of the pouch 2492 in FIG. 24B. The data fields include: the name of patient 2496*a*; a bar code 2496*b*; the address of the facility that filled the pouches with tablets 2496*c*; and the telephone number 2496*d* for additional information. The illustrative bar code associates the tablets in the foldable box with a particular patient. The illustrative seven-day strip 2490 is then placed in an illustrative seven-day container. These illustrative containers are then placed in a secondary container.

Referring to FIGS. 25A-25G there is shown an illustrative label of the type that would be affixed to a secondary container. The label 2500 may be affixed separately or the label may be printed directly on the cardboard or may be printed as a label that is separately affixed.

The illustrative label 2500 comprises a plurality of printed text that may include: the patient's name 2540, the interval during which the medications are taken, e.g. morning, a picture of the patient 2542, patient number 2544, order number 2546, a list of precautions 2548, a listing of the medications 2550, a listing of the time interval for taking the medications 2552, a prescription number 2554, quantity of tablets 2556 per prescription, quantity of refills 2558, length of prescription 2560, the prescribing physician 2562, the manufacturer of the tablets 2564, and the lot number 2566 corresponding to each tablet. Additionally, a picture 2568 of each tablet is provided and the dosage concentration 2570 is provided for each medication. Information about the associated generic drug 2572 is also provided. Furthermore, an expiration date may also be provided for each tablet or for each prescription. Further still, information regarding the generic or trademarked name of the medication may be provided, manufacturer information, corresponding "expiration dates," personal contact information, physician contact information, insurance information, and other such information associated with the tablets in each container.

Further yet, a bar code 2574 provides a means for associating the medications in the foldable box with a particular patient. Alternative means for associating the medications in the box to the patient include, by way of example but not of limitation, the patient's name, a serial number, a radio frequency identification (RFID) tag, or any other such method for associating an individual with a particular item.

Integrated labeling may also include a Patient Information Booklet that includes a plurality of information relating to the patient's prescription order. The Patient Information Booklet may include specific information regarding the medications that a patient is taking, and may also include information specific to the patient, including information about the disease(s) for which the patient is being treated, or information about the mechanism of one or more drugs in the order as it pertains to the specific patient.

Figure 26:
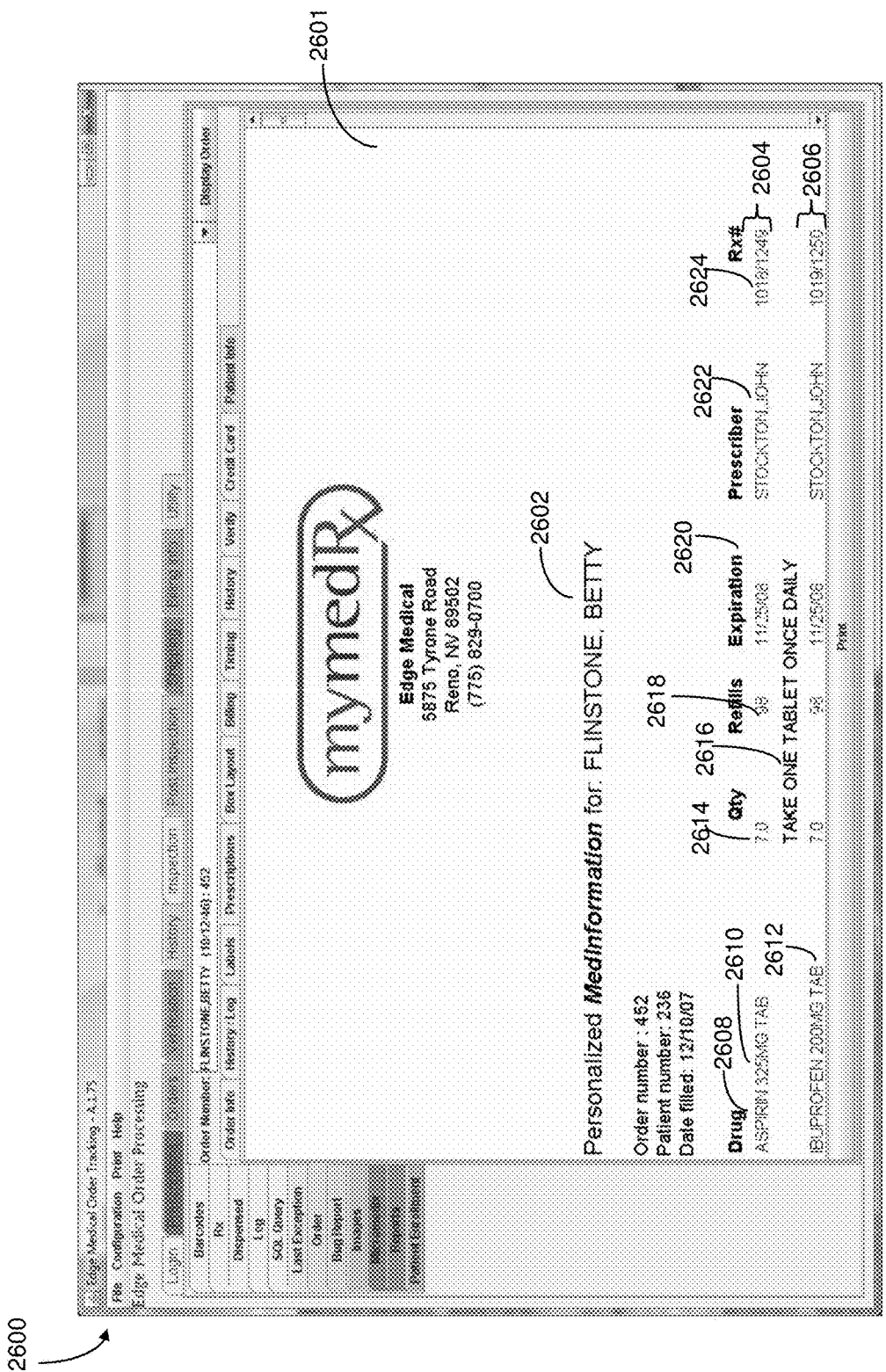
FIG. 26 shows an illustrative GUI including a portion of the Patient Information Booklet before printing.

Referring now to FIG. 26, an illustrative GUI 2600 is shown. Visible in the display window 2601 is a portion of the drug summary that will appear in the patient information booklet that is associated with a patient's prescription order. The patient name 2602 appears near the top of the summary page. Illustrative drug descriptions 2604 and 2606 include information such as drug name 2608, dosage 2610, dosage form 2612, quantity 2614, administration information 2616, number of refills 2618, expiration date 2620, prescriber name 2622, and prescription number 2624.

The inspection process must be performed at about the same time as the labeling and filling processes. The inspection not only verifies that each prescription in the order is correctly filled; it also verifies that the labeling information is correct and is correctly associated with the appropriate patient and prescription order. Further, since the prescription order will typically be dispensed in a compliance container similar to those described above, the labeling information must also accurately reflect the time period for administration of each drug. Further still, the integrated labeling must also accurately reflect the patient information. All of this information must be confirmed during the inspection process.

Figure 27:
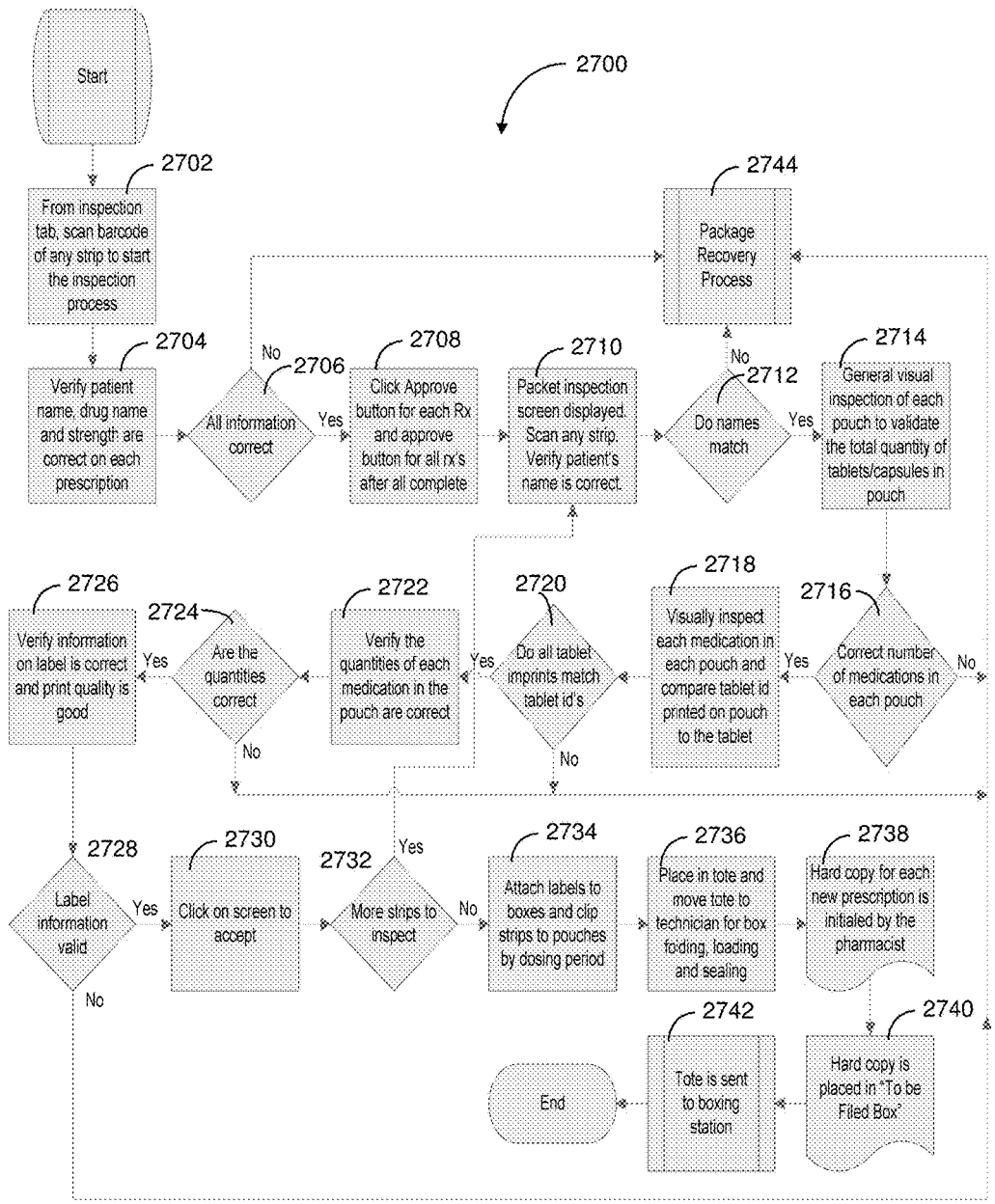
FIG. 27 shows a flowchart of one illustrative embodiment of the inspection process.

One embodiment of the inspection process is shown in the illustrative flowchart of method 2700 in FIG. 27. At block 2702, the inspection process is initiated by scanning a bar code of the label affixed to any strip, after the inspection tab is selected in EPPA. The inspection process includes an initial inspection, which is a secondary validation of drug name, strength, directions, and patient name, at block 2704. The method then proceeds to decision diamond 2706, where it is determined if all information is correct. If any of the information is incorrect, the method proceeds to block 2744, where the package is removed from the inspection process and placed into the package recovery process.

If the information is correct, the method proceeds to block 2708, where the approval of each prescription individually and of the entire prescription order takes place. The method then proceeds to block 2710, where any strip in the order is scanned and the patient's name is verified. Moving on to decision diamond 2712, if the patient's name is not correct, the method proceeds to block 2744, where the package is removed from the inspection process and placed into the package recovery process.

If the patient's name is correct, the method proceeds to block 2714, where a visual inspection takes place to verify that each pouch or cup holds the correct number of tablets. Moving on to decision diamond 2716, if the number of tablets is not correct, the method proceeds to block 2744, where the package is removed from the inspection process and placed into the package recovery process. The visual inspection may include visual inspection by a qualified operator, machine-vision techniques, or some combination thereof.

If the number of tablets in each pouch or cup is correct at decision diamond 2716, the method proceeds to block 2718, where each type of tablet that appears in the pouches or cups is matched to a portion of its integrated labeling, verifying that the tablets are the correct ones that correspond to the prescription order. Moving on to decision diamond 2720, if one or more tablet imprints do not match, the method proceeds to block 2744, where the package is removed from the inspection process and placed into the package recovery process.

If the tablet imprints match, the method proceeds to block 2722, where the quantity of each tablet type in each cup or pouch is verified. Moving on to decision diamond 2724, if one or more cups or pouches do not contain the correct quantity of each tablet, the method proceeds to block 2744, where the package is removed from the inspection process and placed into the package recovery process.

If the quantities of each drug tablet in each pouch or cup are correct, the method proceeds to block 2726, where the information on the integrated labeling is verified, and the print quality is confirmed to be good. Moving on to decision diamond 2728, if any label information is incorrect, or if the print quality is unacceptable, the method proceeds to block 2744, where the package is removed from the inspection process and placed into the package recovery process.

If the integrated label information is correct and the label information is determined to be of sufficient print quality, the method proceeds to block 2730, where the inspected strip is accepted. The method then proceeds to decision diamond 2732, where it is determined if there are additional strips to process for the prescription order. If there are additional strips to process, the method returns to block 2710, and each additional strip is processed in the manner described above, from block 2710 to decision diamond 2732.

Once there are no more strips to process at decision diamond 2732, the method proceeds to block 2734, where the labels are affixed to the secondary containers, and to the pouches or cups if necessary. The method then proceeds to block 2736, where all items are placed in a tote for further processing, including folding, loading, and/or sealing, as necessary.

The method then proceeds to block 2738, where the handwritten prescription is initialed by a qualified pharmacist. The method then proceeds to block 2740, where the initialed handwritten prescriptions corresponding to the prescription order are filed. The method then proceeds to block 2742, where the tote assembly is forwarded to the boxing station.

The inspection method described above is illustrative and may vary as to details. For example, instead of inspecting each strip one at a time before strips are forwarded to the boxing station, as described above in the method 2700, the qualified pharmacist may instead box each strip as soon as the label is verified, and then place the box into the shipping container. Likewise, the qualified Pharmacist may place the strip into a spiral package or into another type of compliance container or apparatus instead of a box.

Alternatively, the inspection method may include printing the exterior integrated labeling that is subsequently affixed to the box before the strips are approved, but after the order has been verified. Then, the strip inspection takes place, and each strip is matched to the integrated label associated with each box as the strip itself is verified.

What is claimed is:

1. A system for integrating a plurality of prescription tablet orders and labeling the multiple prescription tablet orders, comprising:
    a graphical user interface that receives a first prescription input that corresponds to a first prescription order that includes a first plurality of tablets;
    the graphical interface receiving a second prescription input that corresponds to a second prescription order that includes a second plurality of tablets, wherein the first prescription order tablets are different from the second prescription order tablets;
    a first tablet picture input corresponding to the first prescription input;
    a second tablet picture input corresponding to the second prescription input;
    a first hours of administration (HOA) input corresponding to the first prescription input, wherein the first HOA input includes a first time of day and a first frequency for consuming the first prescription order tablets;
    a second hours of administration (HOA) input corresponding to the second prescription input, wherein the second HOA includes a second time of day and a second frequency for consuming the second prescription order tablets;
    a software module that combines the first prescription input, the second prescription input, the first tablet picture input, the second tablet picture input, the first HOA input, and the second HOA input into an integrated prescription order;
    a filling system that receives the integrated prescription order and fills a plurality of packages, wherein at least one multiple prescription package includes a same time for consuming the first tablet associated with the first plurality of tablets and the second tablet associated with the second plurality of tablets;

an automated inspection module for performing an inspection of each package to identify the first tablet and the second tablet within each package, wherein the automated inspection includes an inspection module that operates at visual wavelengths and analyzes each tablet color and each tablet shape; and an integrated label coupled to a box housing the multiple prescription packages, the integrated label indicating information about the first plurality of tablets and the second plurality of tablets, the information including the first tablet picture, the second tablet picture, and at least one drug precaution instruction corresponding to at least one of the first tablet and the second tablet.

2. The system for integrating a plurality of prescription tablet orders of claim 1, wherein the integrated label includes a bar code associating the prescriptions with a patient.

3. The system for integrating a plurality of prescription tablet orders of claim 1, wherein the first tablet picture and the second tablet picture are color images corresponding to each tablet in the integrated prescription order.

4. The system for integrating a plurality of prescription tablet orders of claim 1, wherein the integrated label further comprises a date when the first plurality of tablets and the second plurality of tablets are to be consumed.

5. The system for integrating a plurality of prescription tablet orders of claim 1, wherein the integrated label includes a tablet name corresponding to each of the first prescription and the second prescription.

6. The system for integrating a plurality of prescription tablet orders of claim 1, wherein the integrated label includes a photograph of a patient.

7. The system for integrating a plurality of prescription tablet orders of claim 1, wherein the integrated label further includes a potential interactions instruction corresponding to at least one of the tablets and at least one other substance.

8. The system for integrating a plurality of prescription tablet orders and labeling the multiple prescription tablet orders of claim 1 wherein the box receives the multiple prescription packages,
the box including,
a top wall having one end fixedly coupled to the box and an opposite end that provides a foldable lid;
a front side wall;
a right-side wall that abuts the front side wall and the top wall;
a back side wall that abuts the right-side wall and the top wall;
a left-side wall that is between the back side wall and the front side wall, the left-side wall configured to abut the top wall;
a bottom wall that abuts the front side wall, the right-side wall, the back side wall, and the left-side wall;
a cavity defined by the front side wall, the right-side wall, the back side wall, the left-side wall and the bottom wall;
a code corresponding to one of the packages, wherein the code also corresponds to the prescription;
an integrated label affixed to the box, wherein the integrated label includes a description of the medications and the code;
wherein the box receives the plurality of packages having the code; and
wherein one of the walls receives the integrated label.

9. A system for integrating a plurality of prescription tablet orders and labeling the multiple prescription tablet orders, comprising:

a graphical user interface that receives a first prescription input that corresponds to a first prescription order that includes a first plurality of tablets;
the graphical user interface receiving a second prescription input that corresponds to a second prescription order that includes a second plurality of tablets, wherein the first prescription order tablets are different from the second prescription order tablets;
a first tablet picture input corresponding to the first prescription input;
a second tablet picture input corresponding to the second prescription input;
a first hours of administration (HOA) input corresponding to the first prescription input, wherein the first HOA input includes a first time of day and a first frequency for consuming the first prescription order tablets;
a second hours of administration (HOA) input corresponding to the second prescription input, wherein the second HOA includes a second time of day and a second frequency for consuming the second prescription order tablets;
a software module that combines the first prescription input, the second prescription input, the first tablet picture input, the second tablet picture input, the first HOA input, and the second HOA input into an integrated prescription order;
a filling system that receives the integrated prescription order fills a plurality of multiple prescription packages, wherein each multiple prescription package includes a code, a same time for consuming the tablets, at least one of the first tablets associated with the first plurality of tablets and at least one of the second tablets associated with the second plurality of tablets;
a box that receives the multiple prescription packages, the box including,
a front side wall;
a right-side wall that abuts the front side wall;
a back side wall that abuts the right-side wall;
a left-side wall that is between the back side wall and the front side wall;
a bottom wall that abuts the front side wall, the right-side wall, the back side wall, and the left-side wall; and
a cavity defined by the front side wall, the right-side wall, the back side wall, the left-side wall and the bottom wall;
an integrated label affixed to the box, wherein the integrated label includes a description of the medications, the first tablet picture, the second tablet picture, the code, and a potential interactions instruction corresponding to at least one of the tablets and at least one other substance;
wherein the box receives the plurality of packages that correspond with the code; and
wherein one of the walls receives the integrated label.

10. The system for integrating a plurality of prescription tablet orders of claim 9, wherein the code includes a bar code associating the prescriptions with a patient.

11. The system for integrating a plurality of prescription tablet orders of claim 9, wherein the integrated label includes a date when the multiple prescription packages are to be consumed.

12. The system for integrating a plurality of prescription tablet orders of claim 9, wherein the integrated label includes a photograph of a patient.

13. The system for integrating a plurality of prescription tablet orders of claim 9, wherein the integrated label includes at least one drug precaution instruction corresponding to at least one of the tablets in the multiple prescription package.

14. The system for integrating a plurality of prescription tablet orders and labeling the multiple prescription tablet orders of claim 9 further comprising an automated inspection module for performing an inspection of each package to identify the first tablet associated with the first plurality of tablets and the second tablet associated with the second plurality of tablets within each package, wherein the automated inspection includes an inspection module that operates at visual wavelengths and analyzes each tablet color and each tablet shape.

15. A method for integrating a plurality of prescription tablet orders and labeling the multiple prescription tablet orders, the method comprising:
   receiving with a graphical user interface a first prescription input that corresponds to a first prescription order that includes a first plurality of tablets;
   receiving with the graphical user interface a second prescription input that corresponds to a second prescription order that includes a second plurality of tablets, wherein the first prescription order tablets are different from the second prescription order tablets;
   receiving a first tablet picture input corresponding to the first prescription input;
   receiving a second tablet picture input corresponding to the second prescription input;
   receiving a first hours of administration (HOA) input corresponding to the first prescription input, wherein the first HOA input includes a first time of day and a first frequency for consuming the first prescription order tablets;
   receiving a second hours of administration (HOA) input corresponding to the second prescription input, wherein the second HOA includes a second time of day and a second frequency for consuming the second prescription order tablets;
   combining with a software module the first prescription input, the second prescription input, the first tablet picture input, the second tablet prescription input, the first HOA input, and the second HOA input into an integrated prescription order;
   enabling a filling system to receive the integrated prescription order and fill a plurality of packages, wherein at least one multiple prescription package includes a same time for consuming the first tablet and the second tablet;
   inspecting each package with an automated inspection module for performing an inspection of the first tablet and the second tablet within each package, wherein the automated inspection includes an inspection module that operates at visual wavelengths and analyzes each tablet color and each tablet shape; and
   generating with the software module an integrated label coupled to a box housing the multiple prescription package, wherein the integrated label provides information about the first plurality of tablets and the second plurality of tablets, the information including the first tablet picture, the second tablet picture, and at least one drug precaution instruction corresponding to at least one of the first tablet and the second tablet.

16. The method of claim 15, further comprising
receiving the multiple prescription packages in the box that includes,
   a front side wall;
   a right-side wall that abuts the front side wall;
   a back side wall that abuts the right-side wall;
   a left-side wall that is between the back side wall and the front side wall;
   a bottom wall that abuts the front side wall, the right-side wall, the back side wall, and the left-side wall; and
   a cavity defined by the front side wall, the right-side wall, the back side wall, the left-side wall and the bottom wall;
associating a code with one of the packages, wherein the code also corresponds to the prescription;
affixing an integrated label to one of the walls of the box, wherein the integrated label includes a description of the medications, the first tablet picture, the second tablet picture, the code, and a potential interactions instruction corresponding to at least one of the tablets and at least one other substance; and
receiving the plurality of packages in the box with the code; and
receiving the integrated label on one of the walls.

17. The method of claim 15, wherein the code includes a bar code associating the prescriptions with a patient.

18. The method of claim 15, wherein the integrated label includes a date when the multiple prescription packages are to be consumed.

* * * * *